United States Patent
McGrath et al.

(10) Patent No.: US 7,879,914 B2
(45) Date of Patent: Feb. 1, 2011

(54) METHODS FOR TREATING VIRAL INFECTIONS USING POLYAMINE ANALOGS

(75) Inventors: Michael S. McGrath, Burlingame, CA (US); Kenneth G. Hadlock, San Francisco, CA (US)

(73) Assignee: Pathlogica LLC, San Francisco, CA (US)

( * ) Notice: Subject to any disclaimer, the term of this patent is extended or adjusted under 35 U.S.C. 154(b) by 1097 days.

(21) Appl. No.: 11/535,001

(22) Filed: Sep. 25, 2006

(65) Prior Publication Data

US 2007/0078187 A1    Apr. 5, 2007

Related U.S. Application Data

(60) Provisional application No. 60/719,573, filed on Sep. 23, 2005.

(51) Int. Cl.
| | |
|---|---|
| *A01N 33/26* | (2006.01) |
| *A01N 33/02* | (2006.01) |
| *A01N 37/52* | (2006.01) |
| *A61K 31/15* | (2006.01) |
| *A61K 31/13* | (2006.01) |
| *A61K 31/155* | (2006.01) |

(52) U.S. Cl. ................ 514/674; 514/664; 514/639; 514/634; 514/632

(58) Field of Classification Search .......... 514/664, 514/639, 674, 634, 632
See application file for complete search history.

(56) References Cited

U.S. PATENT DOCUMENTS

| | | |
|---|---|---|
| 5,037,846 A | 8/1991 | Saccomano et al. |
| 5,242,947 A | 9/1993 | Cherksey et al. |
| 5,541,230 A | 7/1996 | Basu et al. |
| 5,580,715 A | 12/1996 | McGrath et al. |
| 5,639,600 A | 6/1997 | McGrath et al. |
| 5,744,122 A | 4/1998 | McGrath et al. |
| 6,274,630 B1 * | 8/2001 | Bergeron, Jr. ............ 514/667 |
| 6,537,523 B1 | 3/2003 | Shiramizu et al. |
| 6,664,042 B1 | 12/2003 | Posnett et al. |
| 6,924,095 B2 | 8/2005 | McGrath et al. |
| 7,087,648 B1 | 8/2006 | McGrath et al. |
| 7,198,946 B2 | 4/2007 | Marton et al. |
| 2005/0159493 A1 | 7/2005 | McGrath et al. |
| 2005/0256207 A1 | 11/2005 | McGrath et al. |
| 2006/0160087 A1 | 7/2006 | McGrath et al. |
| 2007/0078187 A1 | 4/2007 | McGrath et al. |
| 2008/0262092 A1 | 10/2008 | Hadlock et al. |

FOREIGN PATENT DOCUMENTS

WO          98/17624 A1    4/1998

OTHER PUBLICATIONS

Ruhl et al. 1993, Eukaryotic Initiation Factor 5A is a cellular target of the HIV type 1 Rev activation domain mediating Trans-Activation. The Journal of Cell Biology, vol. 123, No. 6, Part 1, pp. 1309-1320.*
De Clercq 2005, Emerging anti HIV drugs. Exper Opinion Emerging Drugs, vol. 10 No. 2, pp. 241-274.*
Seppänen P et al., Quantitation of methylglyoxal bis(guanylhydrazone) in blood plasma and leukemia cells of patients receiving the drug. Int J Cancer. 26(5):571-6 (1980).
Von Hoff DD; MGBG: teaching an old drug new tricks. Ann Oncol. 5(6):487-93 (1994).
Levine AM, et al., Mitoguazone therapy in patients with refractory or relapsed AIDS-related lymphoma: results from a multicenter phase II trial. J Clin Oncol.15(3):1094-103 (1997).
Knight WA 3rd, et al., Methyl-glyoxal bis guanyl hydrazone (methyl-GAG, MGBG) in lymphoma and Hodgkin's disease. A Phase II trial of the Southwest Oncology Group. Invest New Drugs. 1(3):235-7 (1983).
Warrell RP Jr et al., Effectiveness of methyl-GAG (methylglyoxal-bis[guanylhydrazone]) in patients with advanced malignant lymphoma. Blood. 57(6):1011-4 (1981).
Knight WA 3rd et al., Phase I-II trial of methyl-GAG: a Southwest Oncology Group Pilot Study. Cancer Treat Rep. 63(11-12):1933-7 (1979).
Centers for Disease Control and Prevention. Report of the NIH Panel to Define Principles of Therapy of HIV Infection and Guidelines for the Use of Antiretroviral Agents in HIV-Infected Adults and Adolescents. MMWR 47(RR-5):1-91 (1998).
Pierson T et al., Reservoirs for HIV-1: mechanisms for viral persistence in the presence of antiviral immune responses and antiretroviral therapy. Annu Rev Immunol. 18:665-708 (2000).
Marton LJ et al., Polyamines as targets for therapeutic intervention. Annu Rev Pharmacol Toxicol. 35:55-91 (1995).
Mack KD et al. HIV insertions within and proximal to host cell genes are a common finding in tissues containing high levels of HIV DNA and macrophage-associated p24 antigen expression. J Aquir Immune Defic Syndr. 33(3):308-20 (2003).
Marton, et al., Ann. Rev. Pharm. Toxicol., (1995), 35, 55-91.
Wallace, et al., Amino Acids, (2003), 26, 353-365.
Kaczmarek, et al., Cancer Res., (1992), 52, 1891-1894.
Dunzendorfer, U., et al, Some Aspects of Clearance of Mitoguazone in Cancer Patients and Experimental Cancer Models, Drug Res., (1986), 36, 506-508.
Mihich, E., Pharmacology of Methylglyoxal-bis-(guanylhydrazone) (CH3-G), Cancer Research, (1962), 22, 962-974.
Levin, Robert H., Different Patterns of Remission in Acute Myelocytic Leukemia: A Comparison of the Effects of Methyl-Glyoxal-Bix-Guanylhydrazone and 6-Mercaptopurine, Blood, (1963), 21, 6, 689-698.

* cited by examiner

*Primary Examiner*—Sreeni Padmanabhan
*Assistant Examiner*—Kara R McMillian
(74) *Attorney, Agent, or Firm*—Dennis A. Bennett; Suman R. Mirmira

(57) ABSTRACT

Methods for treating viral infections using polyamine analogs, including mitoguazone (MGBG), are provided. In these methods, polyamine analogs destroy macrophages that act as viral reservoirs, facilitating the destruction of the viruses that dwell within the macrophages. Examples of viral infections that may be treated with the present methods include, but are not limited to, infections from human immunodeficiency viruses. These methods differ from previous methods of treatment using polyamine analogs, wherein the polyamine analogs were administered only as anti-tumor agents.

22 Claims, 12 Drawing Sheets

Killing of CD14+/16+ Monocytes by PBIs

Reduction in HIV proviral load after exposure to PA-001 in vitro

Dose-dependent in vitro killing of cultured monkey monocytes with PA-001

Depletion of CD14+CD16+ monocytes in SIV-infected animals treated with PA-001

Monocyte Depletion in the Lymph Node of PA-001 Treated Animals

Selective Depletion of CD14+CD16+ Monocytes in PA-001 Treated Monkeys,

TREATED

CONTROL

METHODS FOR TREATING VIRAL INFECTIONS USING POLYAMINE ANALOGS

FIELD OF THE INVENTION

This invention relates to the use of polyamine analogs, including mitoguazone (MGBG), in treating viral infections, especially where macrophages act as viral reservoirs for the virus, e.g., human immunodeficiency virus (HIV).

BACKGROUND OF THE INVENTION

It has been known since the 1960s that MGBG exhibits anti-tumor activity in various cancer cells. In fact MGBG was shown to be very effective as an antineoplastic agent, and even produced complete remission in trials involving patients with leukemia. Other cancers that were treated by the administration of MGBG in early studies include breast, esophagus, colon, rectal, and kidney. Unfortunately, the use of MGBG in an anti-cancer regimen proved to be unacceptably toxic, resulting in its gradual withdrawal from clinical trials. See Int. J. Cancer, vol. 26, 571 (1980). In the 1970s and 1980s MGBG underwent a bit of a revival, being tested as an anti-cancer agent in subjects with lymphomas, including Hodgkin's, Non-Hodgkin's and AIDS-related lymphoma. See Annals of Oncology, vol. 5, p. 487 (1994); J. Clinical Onc., vol. 15, no. 3, p. 1094 (1997); Invest. New Drugs, vol. 1, p. 235 (1983); and Blood, vol. 57, no. 6 (1981). Again, however, as used in the anti-cancer regimens involved in these studies, MGBG exhibited significant toxicity. The common focus of all of these studies and trials was the ability of MGBG to act as an anti-tumor agent, a characteristic attributed to its role in the inhibition of the enzyme S-adenosyl-L-methionine decarboxylase which catalyzes the synthesis of spermidine. See, for example, Cancer Treatment Reports, vol. 63, no. 11-12, p. 1933 (1979). None of these studies recognized the potential of MGBG as an antiviral agent.

Human immunodeficiency virus (HIV) causes an infection for which researchers have long sought effective antiviral agents. Patients infected with HIV experience a variable but progressive decline in immune function resulting in clinically apparent opportunistic infections and other diseases. Studies have shown that the long term prognosis in HIV infected patients is dictated by the blood cell level of HIV DNA present at the initiation of infection. As the DNA form is a relatively long lived, mostly host cell DNA integrated form of the virus, this high HIV DNA load suggests that patients who have a larger HIV DNA reservoir do worse clinically that do those with lower levels of HIV DNA.

HIV is an RNA retrovirus, that upon successful infection of a host cell, reverse transcribes its genomic RNA into DNA, which then, in a double stranded form, integrates into susceptible host cells. The major targets for infection in vivo are the CD4 expressing T cells and macrophages. Whereas T cells, upon activation of the HIV DNA into an infectious RNA form, generally get killed, the virus expressing macrophages don't die after infection and likely serve as the long term HIV DNA reservoir in vivo.

At least one study on the HIV reservoir has provided half life estimates of 4 years for infected blood macrophages and less than 2 years for infected T cells. Both values help explain the reason for the failure of highly active antiretroviral therapy (HAART) to clear the virus in vivo. More recently, studies on the HIV DNA sequence in vivo showed that in HIV plasma viral load negative subjects on HAART HIV replication continued to occur in vivo within macrophages but not T cells. Therefore, the longest lived reservoir of HIV in vivo is the macrophage.

Other recent studies have confirmed the long lived nature of HIV infected macrophages in vivo. For example, it has been shown that the ancestral form of HIV in vivo in a patient who died of AIDS related dementia resided within macrophages in the outer membrane covering of the brain (meningeal layer). Viral sequences present in this long lived reservoir gave rise to all of the sequences residing in other portions of the brain as well as the peripherally located seminal vesicles and lymph nodes. Another study has suggested a mechanism for the long lived nature of HIV infected macrophages. This study mapped HIV DNA insertion sites within macrophages in tissues from patients with late stage AIDS. All of the insertion sites were within genes near activation genetic loci that, if activated through an HIV insertional process, would keep the infected macrophages in a persistently activated and essentially immortal state.

Considering that HAART only keeps new cells from becoming infected with HIV, any cell already containing HIV DNA would be resistant to drug effects. It's therefore no surprise that upon discontinuation of HAART most HIV infected patients rapidly develop high HIV plasma viral loads because the reservoir initiates new rounds of primary infection, presumably in part because of the infected macrophage reservoir. Therefore, in order to impact the HIV reservoir, a drug must be able to kill the infected macrophages and have a less toxic effect on normal macrophages.

Many recent studies have focused on trying to identify the phenotype of infected macrophages in blood. For example, it has been shown that in AIDS dementia patients where the infected macrophage is known to circulate in the blood as well as cause disease in vivo, that the pathogenic cell expressed CD14 as well as CD16 and elevated levels of the activation marker, HLA-DR. It has also been shown that this same type of macrophage also expressed the proliferation marker, proliferating cell nuclear antigen (PCNA) and upon transfer into a mouse this macrophage caused an end stage AIDS-like lymphoma. Therefore, pathogenic macrophages associated with HIV infection in general express CD14, elevation of HLA-DR, higher levels of CD16 and PCNA. Within this population of cells resides the blood form of the long lived HIV DNA reservoir. Therefore, if a drug could kill only the pathogenic macrophage population leaving the normal macrophages less effected, it would be expected to also kill the macrophage associated HIV DNA reservoir.

SUMMARY OF THE INVENTION

The present invention is based, at least in part, on the inventors' discovery that polyamine analogs such as MGBG and CG47 can be used to decrease the viral load in a patient by destroying macrophages that act as viral reservoirs. As such, these methods differ from previous methods of treatment using polyamine analogs wherein the polyamine analog was administered only as an anti-tumor agent. Examples of viruses that use macrophages as a viral reservoir include, but are not limited to, immunodeficiency viruses, such as the human immunodeficiency virus type 1 (HIV-1) and type 2 (HIV-2), simian immunodeficiency virus (SIV), and feline immunodeficiency virus (FLV).

In one embodiment of the invention, it provides a method of reducing viral load of an infected subject. The method comprises administering to a subject infected by an immunodeficiency virus a therapeutically effective amount of a polyamine analog whereby reducing the viral load in the subject infected by the immunodeficiency virus, wherein the subject does not have AIDS-associated dementia or AIDS associated lymphoma.

In another embodiment of the invention, it provides a method for treating an immunodeficiency viral infection. The method comprises administering to a subject infected by an immunodeficiency virus a therapeutically effective amount of a polyamine analog and at least one an antiviral agent.

In yet another embodiment of the invention, it provides a pharmaceutical formulation which comprises a polyamine analog, an antiviral agent, and a pharmaceutically acceptable carrier.

In yet another embodiment of the invention, it provides a pharmaceutical kit which comprises a polyamine analog, an antiviral agent, and an instruction for administering of the polyamine analog and the antiviral agent to a subject in need of such treatment.

In yet another embodiment of the invention, it provides a pharmaceutical dosage form which comprises a mixture of a polyamine analog and an antiviral agent in an amount of a single dose suitable to be taken by a subject in need of such treatment.

In yet another embodiment of the invention, it provides a pharmaceutical dosage form which comprises a polyamine analog in an amount of a single dose suitable to be taken by a subject in need of treatment for a viral infection.

In yet another embodiment of the invention, it provides a pharmaceutical dosage form which comprises a polyamine analog in an amount of a single dose suitable to be taken in combination with an antiviral agent.

In yet another embodiment of the invention, it provides a pharmaceutical kit which comprises a polyamine analog and an instruction for administering the analog in combination with an antiviral agent.

In still another embodiment of the invention, it provides a method for preventing the onset of AIDS or conditions secondary to HIV infection. The method comprises administering to a subject infected with human immunodeficiency virus a therapeutically effective amount of a polyamine analog, wherein the subject does not display AIDS or a condition secondary to HIV infection.

DETAILED DESCRIPTION

Figure 1:
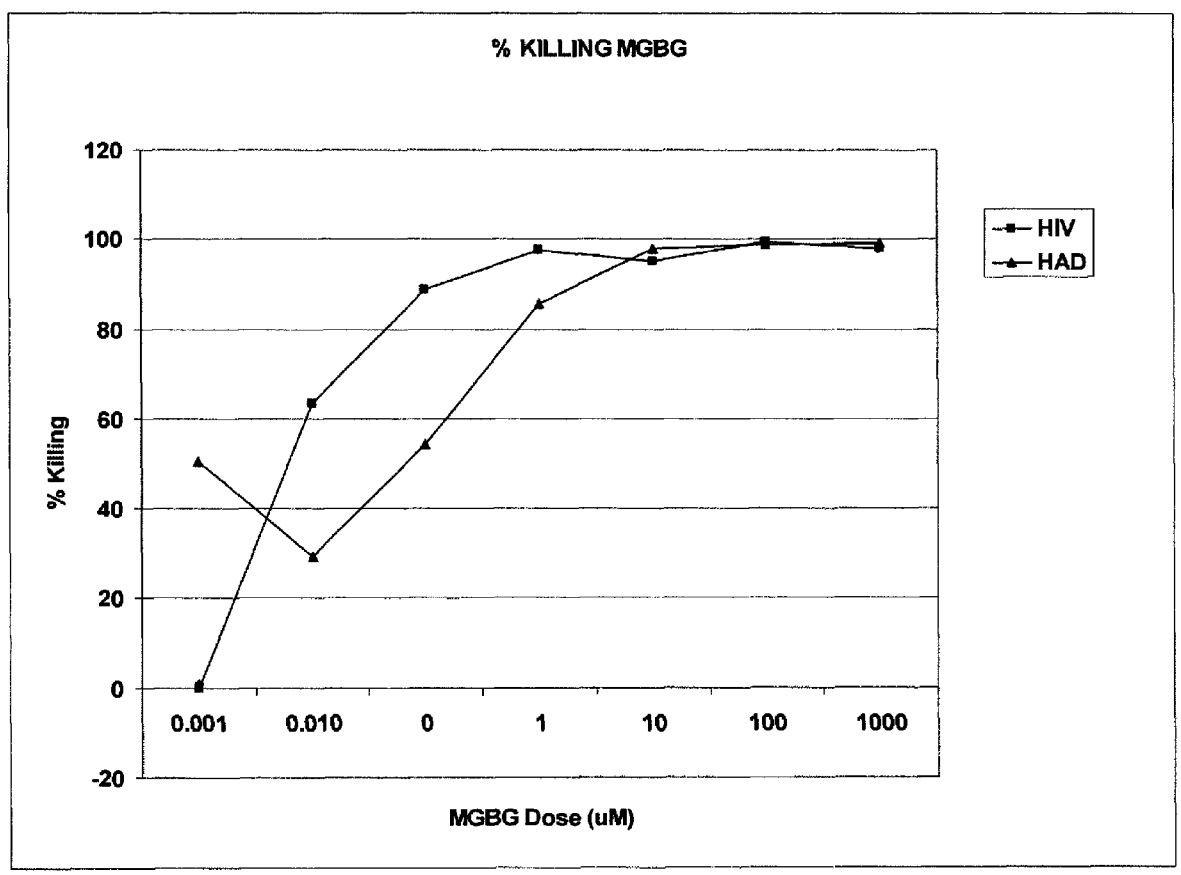
FIG. 1 is a graph illustrating the dose dependent killing of CD14/CD16+ blood macrophages by MGBG. The macrophages were obtained from HIV positive and HIV associated dementia (HAD) patients. The plot shows representative curves from each category.

The present invention is based, at least in part, on the discovery that polyamine analogs such as MGBG and CG47 can be used to decrease the viral load in a patient by destroying macrophages that act as viral reservoirs. As such, these methods differ from previous methods of treatment using polyamine analogs wherein the polyamine analog was administered only as an anti-tumor agent. Examples of viruses that use macrophages as a viral reservoir include, but are not limited to immunodeficiency viruses, such as the human immunodeficiency virus type 1 (HIV-1) and type 2 (HIV-2), simian immunodeficiency virus (SIV), and feline immunodeficiency virus (FLV).

According to one aspect of the invention, it provides methods for reducing viral load, thus treating a subject infected with an immunodeficiency virus, e.g., HIV. In addition, polyamine analogs can be used to prevent the onset of conditions secondary to an immunodeficiency viral infection, e.g., AIDS. In one embodiment, the subject is in the early stage of the viral infection, e.g., has yet to display any condition that is secondary to the viral infection. In another embodiment, the subject is infected with HIV, but does not have AIDS or AIDS associated conditions, e.g., AIDS-associated dementia, AIDS-associated lymphoma such as AIDS-associated non-Hodgkins lymphoma, or AIDS-associated diarrhea. In yet another embodiment, the subject is infected with HIV, but does not have other conditions associated with proliferation or activation of macrophages.

According to the present invention, viral load in a subject infected with an immunodeficiency virus can be reduced by administering to the subject a therapeutically effective amount of a polyamine analog. The therapeutically effective amount of a polyamine analog can be any amount that is sufficient to decrease the subject's viral load of the immunodeficiency virus, e.g., in blood CD14+ and CD16+ macrophages, typically by about 40%, 50%, 60%, 70%, 80%, 90% or more. In one embodiment, the therapeutically effective amount of polyamine analog is an amount that is sufficient to decrease the subject's viral load of the immunodeficiency virus, e.g., in blood CD14+ and CD16+ macrophages by 80% or more. In another embodiment, the therapeutically effective amount of a polyamine analog is an amount that is sufficient to decrease the viral load of the immunodeficiency virus, e.g., in blood CD14+ and CD16+ macrophages by 80% or more while it does not significantly affect normal macrophages in the treated subject.

The optimal dose, frequency of administration, and duration of treatment with a polyamine analog which is effective to induce a clinically significant decrease in the number of macrophages (e.g., in blood CD14+ and CD16+ macrophages) infected by a virus or to induce a clinically significant decrease in viral load may vary from subject to subject, depending on the subject's condition, response to the treatment, and the nature of the polyamine analog and the viral infection. The optimal dose and duration of treatment may be best determined by monitoring the subject's response during the course of the treatment. In some instances, the administration of higher doses may permit less frequent administration, and lower doses may require more frequent administration in order to achieve a clinically significant reduction in infected macrophages or viral load. The polyamine analogs may be administered as a single dose or in multiple doses.

By way of non-limiting example, a clinically significant decrease in viral load may be a decrease in viral load of at least about 50% over the course of treatment with one or more polyamine analogs with or without the concurrent administration of one or more antiretroviral agents. This includes embodiments where the decrease in viral load is at least about 80% over the course of the treatment and further includes embodiments where the decrease in viral load is at least about 90, 95, 98 or even 99% over the course of the treatment. The polyamine analog may be administered for a time sufficient to induce a clinically significant decrease in viral load. The time required to induce a clinically significant decrease in viral load may vary from subject to subject and will depend, at least in part, on the amount and frequency of dosing.

The subject's response to the administration of a polyamine analog may be monitored by measuring the subject's viral load in blood macrophages (CD14+ and CD16+) at various points before, during and/or after the administration of the polyamine analog. In some embodiments, a baseline (pre-treatment) viral load is measured prior to the administration of the polyamine analog, desirably, no more than about one or two days before the administration of the polyamine analog. This baseline viral load is used as a standard to monitor and evaluate the polyamine treatment. Viral load may also be measured between doses of polyamine analog, for example, shortly before each dose is administered. If a subject is taking antiviral or antiretroviral agents in combination with a polyamine analog, some of the viral load reduction may be attributed to the antiviral or antiretroviral agents, however, in the present methods, the synergy between the one or more polyamine analogs and those antiviral or antiretroviral agents produces a decrease in viral load that is greater than the decrease in viral load that the subject would experience using the antivirals or antiretrovirals alone.

Techniques for measuring the viral load in a subject are known and widely available. A description of the various method for measuring viral loads in HIV-infected subjects may be found in "Report of the NIH to Define Principles of Therapy of HIV Infection," Morbidity and Mortality Weekly Reports, Apr. 24, 1998, vol. 47, no. RR-5, revised Jun. 17, 1998. As noted above, two useful techniques for measuring HIV viral load are PCR and bDNA tests. In some instances the subject will have an HIV viral load before treatment with the polyamine analog of about 10,000 to 50,000 copies of RNA/ml of plasma. This is the level at which antiretroviral therapy is typically recommended. However, a starting viral load in this range is not required.

Generally, a therapeutically effective dose of polyamine analog in accordance with the present methods will be one or more doses of from about 10 to about 1100 mg/m$^2$. Lower dose regiments include doses of 10-200, 10-100, 10-50 and 20-200 mg/m$^2$. Higher dose regimens include 200-400, 250-500, 400-600, 500-800 600-1000 and 800-1100 mg/m$^2$. In one embodiment, the dose regimens range from 200-400 mg/m$^2$. In another embodiment, the dose regimens range from 250-500 mg/m$^2$. In yet another embodiment, the dose regimens range from 600-1000 mg/m$^2$. In some embodiments the polyamine analog is administered daily, once per week, once every other week, or once per month. In one embodiment, a dose regimen ranging from 200-400 mg/m$^2$ is administered once a week. In another embodiment, a dose regimen ranging from 250-500 mg/m$^2$ is administered once every other week. The doses may be constant over the entire treatment period, or they may increase or decrease during the course of the treatment. In one embodiment, the treatment is administered once a week and starts with the administration of 200 mg/m$^2$ and increases to 300 mg/m$^2$ and 400 mg/m$^2$ in the second and third weeks, respectively. In another embodiment, the treatment is administered once every other week and is kept constant for the entire duration of treatment with the administration of 250 mg/m$^2$. The doses of polyamine may be administered for at least 1 week, at least two weeks, at least three weeks, at least four weeks, at least 6 weeks, or even at least 8 weeks. Adjusting the dose of polyamine analog within these ranges for a particular subject is well within the skill of the ordinary clinician.

The polyamine analogs may be administered via any conventional route normally used to administer a medicament including, but not limited to, intravenous routes, parenteral routes (e.g., intradermal, intramuscular or subcutaneous routes), oral routes and nasal routes. The polyamine analog may be administered as a pharmaceutical composition in a variety of forms including, but not limited to, liquid, powder, suspensions, tablets, pills, capsules, sprays and aerosols. The pharmaceutical compositions may include various pharmaceutically acceptable additives including, but not limited to, carriers, excipients, binders, stabilizers, antimicrobial agents, antioxidants, diluents and/or supports. Examples of suitable excipients and carriers are described, for example, in "Remington's Pharmaceutical Sciences," Mack Pub. Co., New Jersey (1991). In some embodiments, the polyamine analog may be administered via an IV infusion in an aqueous sugar solution. The polyamine analog may also be associated with another substance that facilitates agent delivery to macrophages, or increases specificity of the agent to macrophages. For example, an agent(s) may be associated into liposomes. Liposomes are known in the art. The liposomes in turn may be conjugated with targeting substance(s), such as IgGFc receptors.

According to the present invention, any polyamine analog is suitable for use in methods provided by the present invention. In one embodiment, the polyamine analogs used in the present invention include compounds of the structures 1, 2, 3, 4, and 5, and the corresponding stereoisomers, salts, and protected derivatives thereof:

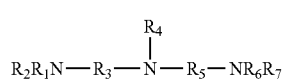

1 where $R_1$, $R_2$, $R_4$, $R_6$ and $R_7$ are independently selected from the group consisting of hydrogen, alkyl and aryl, and where $R_3$ and $R_5$ are alkyl groups;

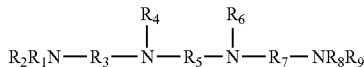

where R1, R2, R4, R6, R8, and R9 are independently selected from the group consisting of hydrogen, alkyl and aryl and where R3, R5 and R7 are alkyl groups;

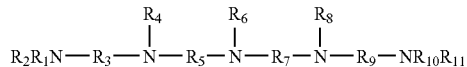

where $R_1$, $R_2$, $R_4$, $R_6$, $R_{10}$ and $R_{11}$ are independently selected from the group consisting of hydrogen, alkyl and aryl, and where $R_3$, $R_5$, $R_7$ and $R_9$ are alkyl groups;

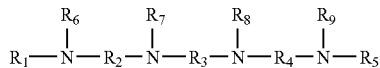

where $R_1$ and $R_5$ are independently selected from the group consisting of methyl, ethyl, n-propyl, and isopropyl;
where $R_2$, $R_3$, and $R_4$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl;
and where $R_6$, $R_7$, $R_8$ and $R_9$ are independently selected from the group consisting of H, methyl, and ethyl;

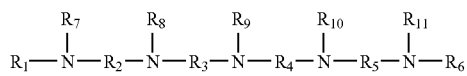

where $R_1$ and $R_6$ are independently selected from the group consisting of methyl, ethyl, n-propyl, and isopropyl;
$R_2$, $R_3$, $R_4$ and $R_5$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ aryl-$C_1$-$C_6$ alkyl;
and where $R_7$, $R_8$, $R_9$, $R_{10}$ and $R_{11}$ are independently selected from the group consisting of H, methyl, and ethyl.

In another embodiment, the polyamine analogs are compounds of the structures 2 and 3, where $R_3$, $R_5$, $R_7$ and $R_9$ are independently $(CH_2)_x$ groups, where x is an integer from 2 to 6, and further where $R_4$, $R_6$ and $R_8$ are hydrogen atoms.

In yet another embodiment, the polyamine analogs are compounds of the structures 2 and 3, where $R_3$, $R_5$, $R_7$ and $R_9$ are independently $(CH_2)_x$ groups, where x is an integer from 2 to 6, and where $R_4$, $R_6$ and $R_8$ are hydrogen atoms, and where $R_1$ and $R_{10}$ are alkyl groups, and further where $R_2$ and $R_{11}$ are hydrogen atoms.

In yet another embodiment, the polyamine analogs are compounds of the structures 2 and 3, where $R_3$, $R_5$, $R_7$ and $R_9$ are independently $(CH_2)_x$ groups, where x is an integer from 2 to 6, and where $R_4$, $R_6$ and $R_8$ are hydrogen atoms, and where $R_1$ and $R_{10}$ are alkyl groups, and where $R_2$ and $R_{11}$ are hydrogen atoms, and further where the polyamine analogs have a molecular weight less than 500.

Further embodiments of compounds of the structure 4 include those where $R_6$, $R_7$, $R_8$ and $R_9$ are H;
where $R_1$ and $R_5$ are ethyl;
where $R_6$, $R_7$, $R_8$ and $R_9$ are H and $R_1$ and $R_5$ are ethyl;
and/or where $R_2$ and $R_4$ are independently selected from the group consisting of $C_1$-$C_6$ alkyl and $R_3$ is selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl.

Additional polyamine analogs useful in the present invention include compounds of the formula 6, and the corresponding stereoisomers, salts, and protected derivatives thereof:

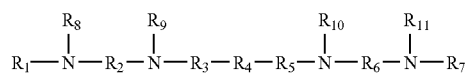

where $R_4$ is $C_2$-$C_6$ n-alkenyl, $C_3$-$C_6$ cycloalkyl, $C_3$-$C_6$ cycloalkenyl, or $C_3$-$C_6$ aryl;
$R_3$ and $R_5$ are independently chosen from a single bond, $C_1$-$C_6$ alkyl, or $C_1$-$C_6$ alkenyl;
$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;
$R_1$ and $R_7$ are independently chosen from H, $C_1$-$C_6$ alkyl, or $C_2$-$C_6$ alkenyl; and
$R_8$, $R_9$, $R_{10}$, and $R_{11}$ are H.

In certain embodiments of the compounds of formula 6, $R_1$ and $R_7$ are independently chosen from $C_1$-$C_6$ alkyl or $C_2$-$C_6$ alkenyl.

Additional polyamine analogs useful in the present invention include compounds of the formula 7, and the corresponding stereoisomers, salts, and protected derivatives thereof:

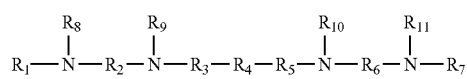

where $R_4$ is $C_1$-$C_6$ n-alkyl or $C_1$-$C_6$ branched alkyl;
$R_3$ and $R_5$ are independently chosen from a single bond or $C_1$-$C_6$ alkyl;
$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;
$R_1$ and $R_7$ are independently chosen from H, $C_1$-$C_6$ alkyl, or $C_2$-$C_6$ alkenyl; and
$R_8$, $R_9$, $R_{10}$, and $R_{11}$ are H.

In certain embodiments of the compounds of formula 7, $R_2$ and $R_7$ are independently chosen from $C_1$-$C_6$ alkyl or $C_2$-$C_6$ alkenyl, $R_4$ is $C_1$-$C_6$ saturated n-alkyl or $C_1$-$C_6$ saturated branched alkyl, and $R_3$ and $R_5$ are independently chosen from a single bond or $C_1$-$C_6$ saturated n-alkyl.

In yet another embodiment, the polyamine analog of the present invention is 1,1'-[methylethanediylidene]dinitrilo) diguanidine (MGBG), 1,11-bis(ethyl)norspermine; 1,8-bis (ethyl)spermidine (BES); 1,12-bis(ethyl)spermine (BES); $N^1$,$N^{12}$-diethylspermine (DESPM); 1,11-bis(ethylamino)-4, 8-diazaundecan-(BE-3-3-3); 1,14-bis(ethylamino)-5,10-diazatetradecane (BE-4-4-4); Diethylhomospermine, $N^1$,$N^{14}$-diethylhomospermine (DEHOP or DEHSPM); diethylnorspermine (DENOP); 1,19-bis(ethylamino)-5,10,15-triaza-nonadecane (BE-4-4-4-4); N-ethyl-N'-(2-(3'-ethylamino-propylamino methyl)-cis-cyclopropylmethyl)- propane 1,3-diamine tetrahydrochloride (SL-11037); N-ethyl-N'-(2-(3'-ethylamino-propylamino methyl)-trans-cyclobutylmethyl)-propane 1,3-diamine tetrahydrochloride (SL-11038); N-ethyl-N'-(2-(3'-ethylamino-propylamino methyl)-trans-cyclopropylmethyl)-propane 1,3-diamine tetrahydrochloride (SL-11044); N,N'-bis(3-ethylaminopropyl)-cis-but-2-ene-1,4-diamine tetrahydrochloride (SL-11047 or CG47), or any two or more combinations thereof. These and other suitable polyamine analogs are described in PCT Patent Application Publication No. WO 99/21542, the entire disclosure of which is incorporated herein by reference.

In still another embodiment, the methods of the present invention employ the polyamine analog of MGBG. For example, as demonstrated in experiments provided herein MGBG can be used to kill, in vitro, blood pathogenic macrophages, e.g., CD14+ and CD16+ macrophages from patients with advanced HIV disease in a dose dependant manner or to kill pathogenic macrophages and reduce viral load in vivo in monkey models infected with SIV. In another embodiment, the methods of the present invention employ the polyamine analog of CG47, e.g., to kill blood derived HIV DNA containing macrophages.

Without being limited to any technical detail, applicants believe that the role of the polyamine analogs is to kill pathogenic macrophages to prevent the establishment and maintenance of viral reservoirs, thereby exposing the virus and, in some instances, allowing other antiviral agents, which may be administered in combination with the polyamine analogs, to access and destroy the viruses that dwell within the macrophage reservoirs.

According to another aspect of the invention, it provides methods for reducing viral load and/or treating viral infection of an immunodeficiency virus by administering to an infected subject a therapeutically effective amount of a polyamine analog and at least one antiviral agent. In one embodiment, the antiviral agent is an antiretroviral agent, e.g. nucleoside reverse transcriptase inhibitors, nucleotide reverse transcriptase inhibitors, non-nucleoside reverse transcriptase inhibitors, protease inhibitors, entry inhibitors, integrase inhibitors or gp41, CXCR4, or gp120 inhibitors. Examples of nucleoside reverse transcriptase inhibitors for the treatment of HIV infections include amdoxovir, elvucitabine, alovudine, racivir (±-FTC), phosphazide, fozivudine tidoxil, apricitibine (AVX754), amdoxovir, zidovudine (AZT), didanosine (ddI), lamivudine (3TC), stavudine (d4T), zalcitabine (ddC), emtricitabine (FTC), and abacavir (ABC). Examples of nucleotide reverse transcriptase inhibitors include tenofovir (TDF) and adefovir. Examples of non-nucleoside reverse transcriptase inhibitors include capravirine, emivirine, calanolide A, etravirine, efavirenz (EFV), nevirapine (NVP) and delavirdine (DLV). Examples of protease inhibitors include amprenavir (APV), tipranavir (TPV), lopinavir (LPV), fosamprenavir (FPV), atazanavir (ATV), darunavir, brecanavir, mozenavir, indinavir (IDV), nelfinavir (NFV), ritonavir (RTV), and saquinavir (SQV). Examples of entry inhibitors include SP01A. Examples of a HIV integrase inhibitor include curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518, BMS-538158, GSK364735C, Examples of a gp41 inhibitor include enfuvirtide (ENF). Examples of a CXCR4 inhibitor include AMD-070, Examples of a gp120 inhibitor include BMS-488043.

In another embodiment, the polyamine analog is administered concurrently with a highly active antiviral therapy (HAART), i.e., a combination of a protease inhibitor, a non-nucleoside reverse transcriptase inhibitor and a nucleoside reverse transcriptase inhibitor, or a combination of two non-nucleoside reverse transcriptase inhibitors and a nucleoside reverse transcriptase inhibitor. In general, the polyamine analog may be administered simultaneously or sequentially (i.e., before or after) with the administration of antiviral or antiretroviral agents. Administration of the antiviral and antiretroviral agents to subjects in need thereof can be made in accordance with regimens and dosages well known in the art.

In yet other embodiments, the antiviral agent is an agent that is capable of reducing the immunodeficiency viral load in T-cells. T-cells, particularly CD4+ T-cells, also serve as a viral reservoir for immunodeficiency viruses such as HIV. Thus, combination treatments of polyamine analogs with agents that reduces the immunodeficiency viral load in T-cells are particularly desirable for flushing or destroying viral reservoirs of immunodeficiency virus. Suitable agents that reduce the immunodeficiency viral load in T-cells are reviewed in Pierson et al. (Annu. Rev. Immunol. (2000), 18:665-708) and include, without any limitation, T-cell activating cytokines, anti-CD3 antibodies, and anti-CD45RO-toxin conjugates. For example, T-cell activating cytokine such as IL-2, IL-6, TNF-α, and any two or more combinations thereof may be used in the present methods.

According to another aspect of the present invention, it provides pharmaceutical compositions, pharmaceutical dosage forms, pharmaceutical kits suitable to be used to reduce viral load and/or treat viral infection, e.g., according to the methods provided by the present invention.

In one embodiment, the present invention provides a pharmaceutical formulation comprising one or more polyamine analogs, one or more antiviral agents, and a pharmaceutically acceptable carrier.

In another embodiment, the present invention provides a pharmaceutical kit comprising one or more polyamine analog, and optionally one or more antiviral agent, and an instruction for administering of the polyamine analog and/or the antiviral agent to a subject in need of such treatment. For example, the instruction can contain information with respect to therapeutic indication of the agents contained in the kit, dosage and administering regimen with respect to one or more agents, timing of taking the therapeutic agents contained in the kit, duration of the treatment, etc.

In yet another embodiment, the present invention provides a pharmaceutical dosage form comprising a mixture of polyamine analog and an antiviral agent in an amount of a single dose suitable to be taken by a subject in need of such treatment. For example, a single dosage can be a unit dosage, which can be taken in one or more units at a time. Alternatively a single dosage can be an amount suitable to be taken at a regular time interval, e.g., every day, every two, three, four, five, or six days, every week, etc.

In still yet another embodiment, the present invention provides a pharmaceutical dosage form comprising a polyamine analog in an amount of a single dose, e.g., unit dose suitable to be taken by a subject in need of treatment for a viral infection or in combination with an antiviral agent. For example, in general a single dosage form of a polyamine analog suitable for reducing viral load or treating viral infection, with or without an antiviral agent is about 250-500 mg/m$^2$.

According to the present invention, polyamine analogs of the present invention can be formulated with conventional carriers and excipients, which can be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients, e.g., polyamine analogs to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention, e.g., polyamine analogs together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl n-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The following definitions and methods are provided for the purpose of assisting those of ordinary skill in the art to the practice the present invention.

Definitions

A "polyamine" is any of a group of aliphatic, straight-chain amines derived biosynthetically from amino acids; polyamines are reviewed in Marton et al. (1995) Ann. Rev. Pharm. Toxicol. 35:55-91. By "polyamine" is generally meant a naturally-occurring polyamine or a polyamine which is naturally produced in eukaryotic cells. Examples of polyamines include putrescine, spermidine, spermine and cadaverine.

A "polyamine analog" is an organic cation structurally similar but non-identical to naturally-occurring polyamines such as spermine and/or spermidine and their precursor, diamine putrescine. Polyamine analogs can be branched or un-branched, or incorporate cyclic moieties. See, for example, WO 98/17624 and U.S. Pat. No. 5,541,230. U.S. Pat. Nos. 5,037,846 and 5,242,947 disclose polyamines comprising primary amino groups. In some embodiments, all the nitrogen atoms of the polyamine analogs are independently secondary, tertiary, or quaternary amino groups, but are not so limited. Polyamine analogs may include imine, amidine and guanidine groups in place of amine groups. As used herein, the term "polyamine analog" should be understood to include stereoisomers, salts and protected derivatives of polyamine analogs.

A "subject" may be any animal suffering from a viral infection that is treatable in accordance with the present methods. An animal is a living multicellular vertebrate organism, and includes both human and non-human mammals.

MGBG is 1,1'[methylethanediylidene]dinitrilo)diguanidine and is also known as methylglyoxal bis(guanylhydrazone), methyl-GAG, and mitoguazone. As used herein, MGBG includes the free base and salts thereof. It is commonly, but not necessarily, used as a dihydrochloride.

A "macrophage" is a phagocytic cell, some are fixed and other circulate in the blood stream. Macrophages are regulatory and effector cell of the immune response. These cells are susceptible to infection by viruses. As used herein, the terms "macrophage" and "monocyte" are used interchangeably, as it is understood that in the art the term "monocyte" is often used to describe a circulating mononuclear cell that expresses the CD14 cell surface marker, and when in a tissue this cell is also classified as a macrophage.

A "macrophage-associated disease" is a disease, disorder, or indication, other than an immunodeficiency viral infection, that is associated with an elevated or abnormal level of macrophage proliferation or activation as compared to control sample(s). Such disorders include, but are not limited to, AIDS-associated dementia, Alzheimer's disease (AD), Amyotrophic Lateral Sclerosis (ALS) AIDS lymphoma, follicular lymphoma, mycoses fungoides, T cell and B cell lymphomas with significant macrophage compartments, age related macular degeneration (ARMD), wet and dry forms, atherosclerosis, kidney disease such as focal segmental glomerulosclerosis, and membrane proliferative glomerulo nephropathy, lupus, psoriaform dermatitis, AIDS-associated diarrhea, prelymphomatis autoimmune disease such as AILD (angioimmunoblstic lymphadenopathy with dysproteinemia), chronic hepatitis viral diseases (HBV and HCV), peripheral sensory neuropathy associated with HIV infection or diabetes mellitus and herpes virus associated diseases such as Castleman's disease and Kaposi's sarcoma. In one embodiment, they include invasive breast cancer and pancreatic cancer. The terms "disorder" and "disease" are used interchangeably herein. "Macrophage-associated dementia" is a dementia that is associated with an elevated, or abnormal, level of macrophage proliferation or activation as compared to control sample(s). Such dementias include, but are not limited to, AD. A macrophage-associated disorder, disease or dementia can be HIV-mediated or non-HIV-mediated, or HIV-associated or non-HIV associated. A "non-HIV-mediated" disease or dementia is a disease or dementia which is not caused by HIV, either directly or indirectly. A "non-HIV-associated" disease or dementia is not normally associated with or secondary to HIV infection. An "HIV-mediated" disease, dementia, or indication is directly or indirectly caused by (and/or linked to) HIV infection. An "HIV-associated" disease, dementia or indication is defined more broadly as generally associated with or secondary to an HIV infection; "HIV-mediated" diseases, for example, are included in those considered to be "HIV-associated."

A "virus" is a microscopic infectious organism that reproduces inside living cells. A virus consists essentially of a core of a single nucleic acid surrounded by a protein coat, and has the ability to replicate inside a living cell. The term virus includes retroviruses, which are RNA viruses wherein the viral genome is RNA and lentiviruses which describes a genus of viruses containing reverse transcriptase.

HIV is a retrovirus that causes immunosuppression in humans (HIV disease), and leads to a disease complex known as the acquired immunodeficiency syndrome (AIDS). "HIV disease" refers to a well-recognized group of signs and symptoms in persons infected by an HIV virus.

"Viral load" is a measure of the severity of a viral infection, and can be estimated by calculating the amount of virus in a body fluid or in infected cells. Viral load may employed as a surrogate marker for disease progression. Viral load is typically measured by PCR and bDNA tests and is generally expressed in number of virus copies or equivalents per milliliter. For example, "HIV viral load" may be measured by determining the level of HIV-RNA (measured in copies per ml) detectable by polymerase chain reaction (PCR) in the plasma of an HIV-infected subject.

A "clinically significant" reduction in HIV viral load includes a reduction greater than or equal to about 80% (a half log) relative to a baseline value. Similarly, a "clinically significant" reduction in the number of HIV-infected CD14/CD16+ blood macrophages includes a reduction of at least about 80% relative to a baseline value.

A "pharmaceutical composition" refers to a chemical composition capable of inducing a desired therapeutic or prophylactic effect when properly administered to a subject or a cell.

A "pharmaceutical dosage form" refers to a pharmaceutical composition in a suitable dosage amount, e.g., single dosage and in a form suitable for administration, e.g., tablet, capsule, injectable solution, etc.

A "pharmaceutical kit" refers to a container containing a pharmaceutical composition, e.g., one or more pharmaceutical dosage forms and optionally an instruction for administering the pharmaceutical composition.

"Contacting" includes incubating a compound (e.g., MGBG) with a cell.

An "antiviral agent" is an agent that specifically inhibits a virus from replicating or infecting cells. In one embodiment, an antiviral agent is an antiretroviral agent that specifically inhibits a retrovirus from replicating or infecting cells. For example, an HIV "antiretroviral agent" may refer to any pharmacological, biological or cellular agent that has demonstrated the ability to inhibit HIV replication. In another embodiment, an antiviral agent is an agent capable of reducing viral load in T cells.

A "therapeutically effective amount" is a quantity of a compound (e.g., MGBG or an antiviral agent) that is sufficient to achieve a desired effect in a subject being treated. For instance, this can be the amount necessary to reduce a viral load or to otherwise measurably alter or alleviate the symptoms of a viral infection. For example, a therapeutically effective amount of MGBG used to treat a subject infected with the HIV virus may refer to the amount needed to produce a clinically significant decrease in HIV viral load. A therapeutically effective amount of a compound of the present invention may vary depending upon the route of administration and dosage form. In addition, specific dosages may be adjusted depending on conditions of disease, the age, body weight, general health conditions, sex, and diet of the subject, dose intervals, administration routes, excretion rate, and combinations of drugs.

An "alkyl" is a cyclic, branched, or straight chain chemical group containing carbon and hydrogen, such as methyl, butyl, t-butyl, pentyl, cyclopropyl, and octyl. Alkyl groups can be either unsubstituted or substituted with one or more substituents, e.g., halogen, alkoxy, acyloxy, amino, hydroxyl, mercapto, carboxy, benzyl. Alkyl groups can be saturated or unsaturated (e.g., containing —C=C— or —C≡C— subunits), at one or several positions. Unless otherwise specified, alkyl groups will comprise 1 to 8 carbon atoms, but may include 1 to 6, or even 1 to 4 carbon atoms. "Cycloalkyl" refers to cyclic alkyl groups only, such as cyclopropyl, cyclobutyl, cyclopentyl, etc. "n-alkyl" refers to a linear (i.e., straight-chain) alkyl group only, while "branched alkyl" refers to branched alkyl groups to the exclusion of cyclic and linear alkyl groups. "Alkenyl" refers to a cyclic, branched, or straight chain chemical group containing carbon and hydrogen where at least one bond is monounsaturated, such as ethenyl, cyclopentenyl, or 1,3-butadienyl. Alkenyl groups can be substituted as indicated for alkyl groups. Alkenyl groups can be designated as cyclic, linear (n-alkenyl) or branched in an analogous fashion to the preceding designations for alkyl. An "aryl" is an unsaturated aromatic carbocyclic group having a single ring (e.g., phenyl), or multiple condensed rings (e.g., naphthyl), which can optionally be unsubstituted or substituted with amino, hydroxyl, alkyl, alkoxy, chloro, halo, mercapto and other substituents.

A "stereoisomer" is defined as any optical isomer of a compound, including enantiomers and diastereomers. Unless otherwise indicated, structural formula of compounds are intended to embrace all possible stereoisomers.

A "salt" is defined as a compound formed by the replacement of one or more hydrogen atoms with elements or groups, which is composed of anions and cations, which usually ionizes in water; a salt is formed, for instance, by neutralization of an acid by a base. A polyamine analog salt can comprise, for example, chloride ions.

"Protected derivative" is used to refer to a compound protected with a protecting group. "Protecting group" refers to a chemical group that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Exemplary protecting groups for the amino functionality include, but are not limited to, mesitylenesulfonyl (MesSO$_2$), benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc).

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Exemplary embodiments of the present methods and compositions are provided in the following examples. The following examples are presented to illustrate the methods for treating viral infections and to assist one of ordinary skill in making and using the same. The examples are not intended in any way to otherwise limit the scope of the invention.

EXAMPLES

In the examples that follow, methods for killing CD14/CD16+ cells are illustrated.

Example 1

Procedure/Protocol Followed for Susceptibility Assays

The following procedures/protocols were used in some of the examples that follow. All steps were performed in a biological safety cabinet using Universal Precautions for handling human blood samples and standard aseptic techniques.

Blood was drawn in heparinized tubes (green top Vacutainer tubes from Becton-Dickson) and Percol gradient separated into peripheral blood mononuclear cells (PBMCs), according to the following procedure. Aliquots of no more than 25 mL whole blood were transferred into clean, sterile, prelabeled 50 mL conical tubes. Using a sterile 25 mL pipet, equal volume of PBS ($Mg^{+2}/Ca^{+2}$ free) was added to the whole blood and the tubes were inverted 2 or 3 times. This resulted in a 1:1 dilution of the blood. (For example: 10 mL whole blood +10 mL PBS.)

The Percol (1.087 grams/mL) was made according to the following formulation: 25 mL Percol (Amersham, Piscataway, N.J.), 11 mL Sterile water and 4 mL 10× saline.

The diluted blood was slowly and carefully layered over the sterile Percol in amounts of 15-20 mL by holding the pipet at a 45 degree angle, relative to the Percol tube, and slowly dripping the diluted blood down the side of the tube. The resulting mixture was centrifuged at 2100 RPM for 30 minutes at 25° C. The buffy coat (i.e., the white layer between the yellow plasma on top and clear Percol solution below) so obtained was then slowly aspirated, taking care not to aspirate the Percol. The buffy coat was resuspended in sterile PBS ($Mg^{+2}/Ca^{+2}$ free) and the volume was brought up to 50 mL. The mixture was gently mixed by slowly pipetting up and down 3 times and the cell suspension was centrifuged at 1500 RPM for 10 minutes at 25° C. The supernatant was discarded and the bottom of the tube gently tapped to dislodge the cell pellet.

The PBMC for the susceptibility assays was prepared in accordance with the following procedures. A cell culture medium was prepared by mixing RPMI+10% FBS+1% sodium pyruvate and filter sterilized using a filter unit with 0.22 micron pore size. The cell pellet was then resuspended in 3 ml of the cell culture medium. The suspension was gently mixed by slowly pipetting up and down 3 times. The cells were counted using a hemacytometer and the cell density was adjusted to $1\times10^6$ cells/mL in the cell culture medium, followed by mixing by slowly pipetting up and down 3 times. The cells were incubated in a 50 mL sterile polypropylene tube, at 37° C. and 5% $CO_2$ for 1-2 days. The cap was loosened and the tubes were tipped to 30-45 degrees relative to the tray surface. A styrofoam tube rack was used to hold the tubes.

The MGBG drug was prepared in accordance with the following procedures. A primary stock of MGBG was prepared by weighing out enough MGBG to make a 1 molar (M) solution and dissolved in sterile PBS ($Mg^{+2}/Ca^{+2}$ free). The solution was vortexed until all of the MGBG had dissolved. A secondary stock (0.01 M) was prepared from a 1/100 dilution of the primary stock and filter sterilized by passing the solution through a 0.22 micron filter. A working stock (0.001 M or 1,000 microMolar) was prepared from a 1/10 dilution of the secondary stock. The CG47 drug was prepared by an identical procedure.

Drug doses for the susceptibility assays were prepared in accordance with the following procedures. Drug dilutions were prepared at 10-fold higher concentrations than the final desired concentrations. For example a 100 microMolar drug solution was made for a desired final concentration of 10 microMolar. The drugs were diluted an additional 1/10 upon addition to the cell suspension (e.g., 0.1 mL drug +0.9 mL cell suspension). The drug doses for the susceptibility assays were prepared right before use in cell culture media.

Susceptibility assays were conducted in accordance with the following procedures. The MGBG drug as added 1-2 days after PBMC was separated from whole blood. The PBMC was prepared for the addition of the drug by centrifuging the cell suspension at 1500 RPM for 10 minutes at 25° C., discarding the supernatant, loosening the cell pellet from the bottom of the tube, resuspending the cell pellet in the cell culture medium and gently mixing by slowly pipetting up and down several times.

Aliquots of 0.9 mL of the cell suspension were dispensed into 12×75 mm polypropylene tubes and 0.1 mL of each prepared drug dose was added into the individual tubes. The cells and drug were then incubated for 5 days in 37° C. and 5% $CO_2$.

After the 5 day incubation with and without the drugs, the cells were centrifuged at 1500 RPM for 10 minutes at 25° C. The supernatant was discarded and the cells resuspended in 100 microliters of PBS ($Mg^{+2}/Ca^{+2}$ free) using a Vortex for mixing. Eight microliters of each of: 1) antibodies: CD71-FITC (BD); CD16-PE (Dako); and CD14-PerCP (BD); or 2) antibodies: CD16-FITC (Dako); CD95-PE (Pharmingen); and CD14-PerCP (BD) were then added to the cell suspension. The antibodies and cells were incubated at room temperature, for 20 minutes in the dark. At the end of the incubation period, 1 mL PBS ($Mg^{+2}/Ca^{+2}$ free) was added over the cell suspension and the cell suspension was centrifuged at 1500 RPM for 10 minutes at 25° C. The supernatant was discarded and the residual liquid was blotted onto a clean gauze pad. The cell pellet was resuspended in 0.5 mL of a fixative of paraformaldehyde/PBS ($Mg^{+2}/Ca^{+2}$ free).

Fluorescence emission measurements were obtained with a flow cytometer, using the following instrument settings in BD FACSCAN: 1) Detector: FL1=533 amps; FL2=570 amps; and FL3=550 amps; 2) Threshold=FSC 180; 3) Compensation: FL1 10.5% FL2; FL2 26.1% FL1; FL2 8.3% FL3; FL3 25.4% FL2; 4) Count=50,000 UNgated events.

Example 2

Effect of MGBG on CD14/16+Blood Macrophages Infected with HIV

The present example illustrates the effect of MGBG on CD14/CD16+ blood macrophages from HIV-positive and HIV-associated dementia (HAD) patients. A susceptibility assay (described above) was performed on blood cells from three sets of four patients. Representative curves of percent of CD14/16+blood macrophages killed versus MGBG concentration are reproduced in FIG. 1.

As shown in FIG. 1, MGBG killed the HIV infected macrophages in a dose-dependent manner. Complete killing of CD14/16+ cells that contain HIV DNA was observed at 1 µM of the drug. MGBG was nearly as effective in killing HIV-infected macrophages from HAD patients. This data demonstrates that MGBG causes the destruction of macrophages harboring HIV and should be helpful in eliminating these persistent reservoirs of HIV and thus useful in the treatment of AIDS.

Example 3

Figure 2:
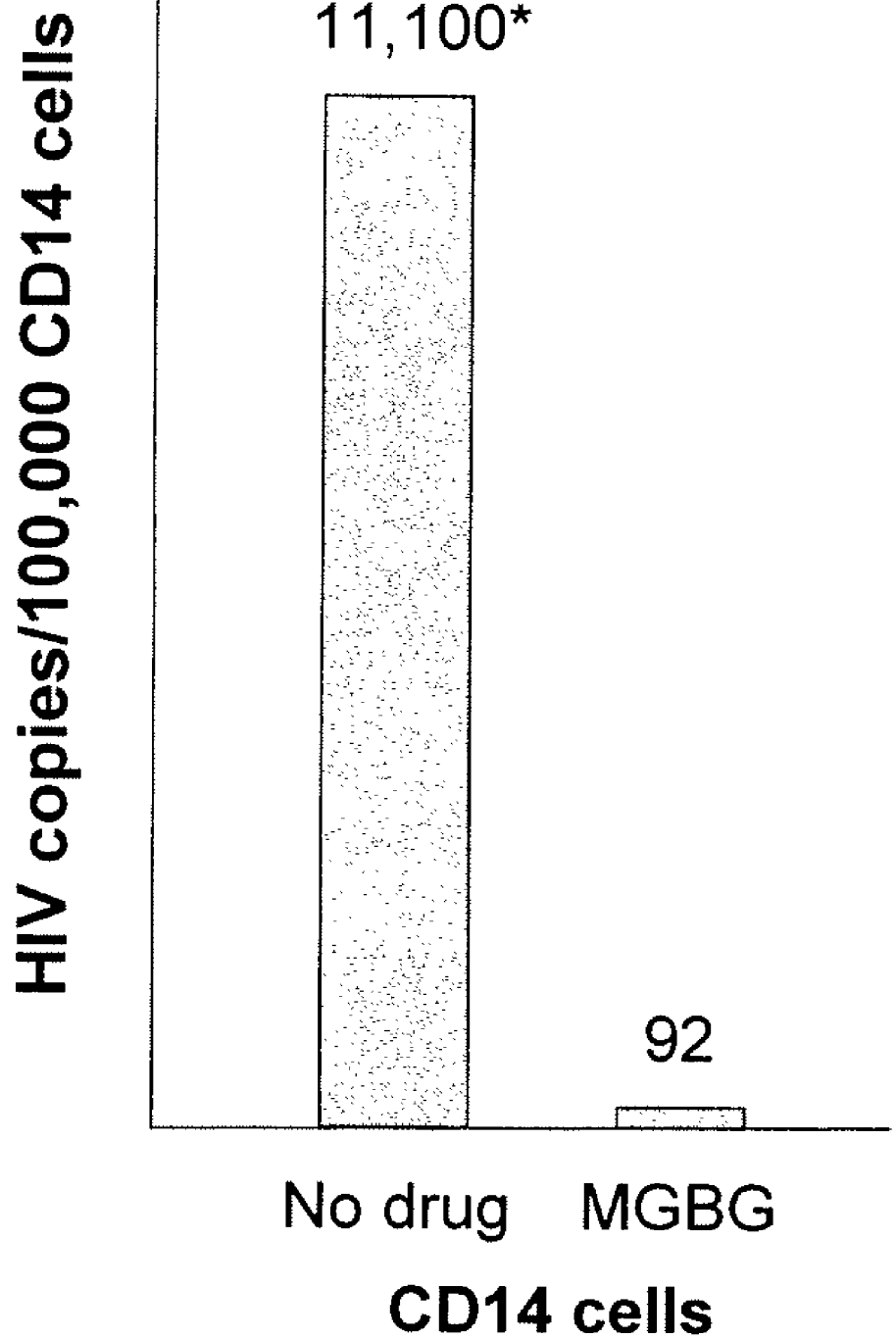
FIG. 2 shows the near quantitative ex vivo killing of HIV DNA-containing CD14/CD16+ blood macrophages by 1 μM MGBG.

Blood from patients with advanced HIV disease was Percol gradient separated into peripheral blood mononuclear cells (PBMCs) and 5 million cells from each specimen were exposed to a 1 µM concentration of MGBG or control saline for five days. Immunophenotypic analysis showed >80% killing of the CD14/CD16 blood macrophage population. After the five day incubation, CD14 immunomagnetic separation with a Miltenyi separation system was performed. Separated CD14 cells from treated and untreated control specimens were evaluated for the level of HIV DNA in each specimen. C-jun, single copy DNA controls were utilized in each specimen to provide the HIV DNA/genomic equivalent values as determined by quantitative DNA PCR analysis as described in Mack, K. D., et al. JAIDS (2003) 33: 308-20. Pretreatment (no drug) values of HIV DNA copy number/100,000 cell equivalents are compared to HIV copy numbers in the treated specimens. All values are for HIV DNA copy numbers in isolated CD14 cell populations. All blood specimens evaluated showed significant reductions in HIV DNA associated with CD14 cells (average >99% reduction), e.g., see FIG. 2.

Example 4

Figure 3:
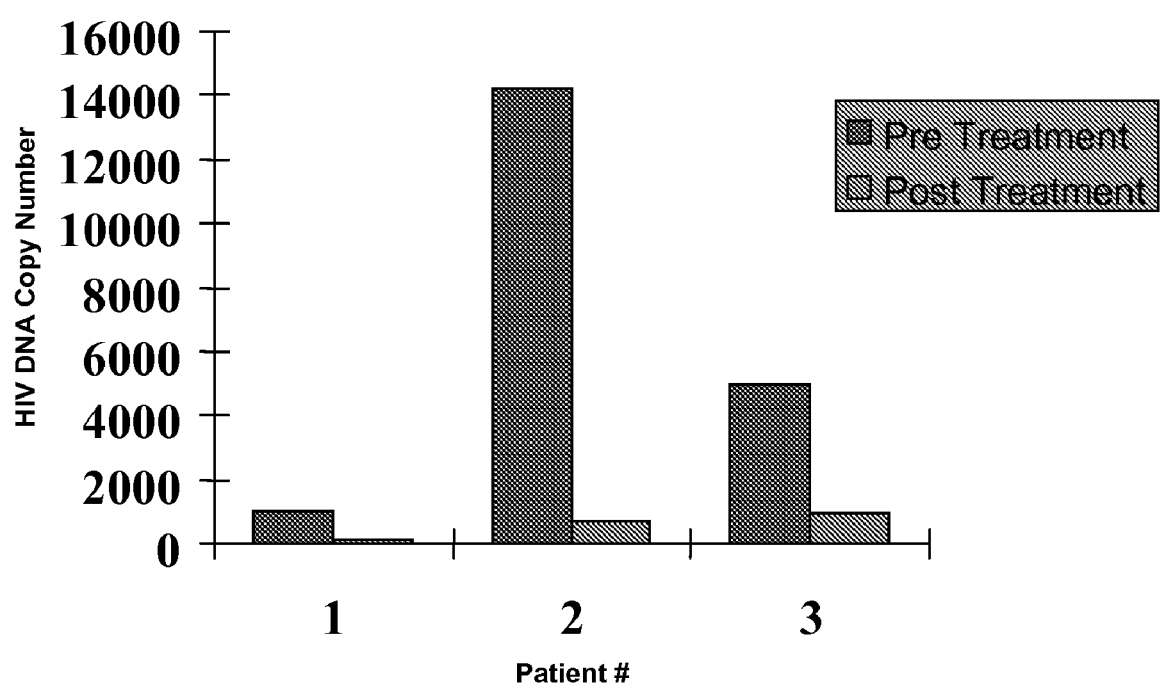
FIG. 3 shows the reductions in HIV DNA associated with CD14 cells in three blood samples collected from patients with HIV infections before and after treatment with the polyamine analog, CG47.

Blood from three patients with advanced HIV disease was Percol gradient separated into peripheral blood mononuclear cells (PBMC's) and 5 million cells from each specimen were exposed to a 10 micromolar concentration of the polyamine analog CG47 or control saline for 5 days. Immunophenotypic analysis showed >80% killing of the CD14/CD16 blood macrophage population. After the 5 day incubation, CD14 immunomagnetic separation with a Miltenyi separation system was performed. Separated CD14 cells from treated and untreated control specimens were evaluated for the level of HIV DNA in each specimen. C-jun, single copy DNA controls were utilized in each specimen to provide the HIV DNA/genomic equivalent values as determined by quantitative DNA PCR analysis as described in Mack et al. (JAIDS). Pretreatment (no drug) values of HIV DNA copy number/100,000 cell equivalents are compared to HIV copy numbers in the treated specimens. All values are for HIV DNA copy numbers in isolated CD14 cell populations. As shown in FIG. 3, all three blood specimens evaluated showed significant reductions in HIV DNA associated with CD14 cells (average >90% reduction).

Example 5

Figure 4:
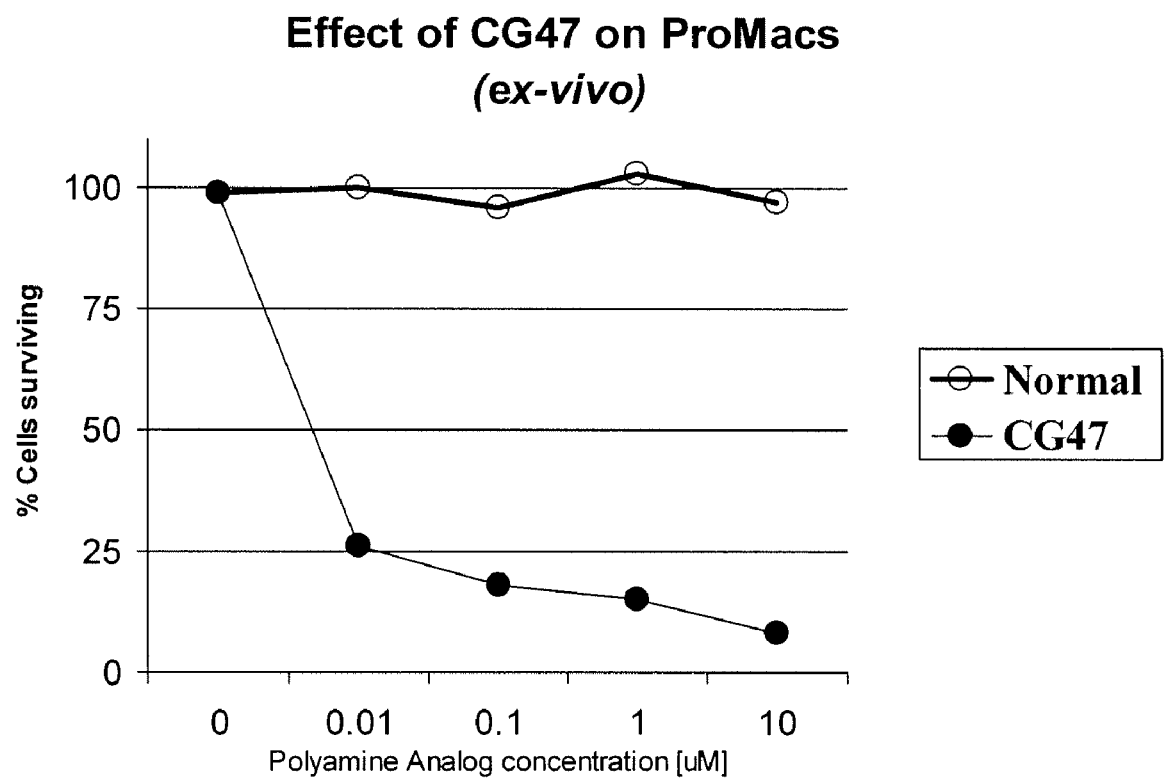
FIG. 4 is a graph illustrating the ex vivo dose dependent killing of CD14/CD16+ blood macrophages by CG47. The macrophages were isolated from an HIV positive patient and a normal patient. The graph shows that the macrophages from the HIV patient were extremely sensitive to CG47 whereas those from the normal patient were essentially unaffected.

The ability of polyamine analogs MGBG and CG47 to kill CD14/CD16+ blood macrophages in HIV infected and normal patients was measured. Blood from normal (uninfected) patients and HIV patients with advanced AIDS was obtained and subjected to a susceptibility assay as described above. Results are shown in Table 1 below and in FIG. 4. As shown in the table, the mean $ED_{50}$ for killing the macrophages by CG47 and MGBG was significantly lower than for normal macrophages, showing a marked selectivity for destruction of the HIV infected macrophages. FIG. 4 displays representative curves illustrating the dose dependent killing of CD14/CD16+ blood macrophages by CG47.

TABLE 1

| Advanced HIV Disease (CG47) | | Advanced HIV Disease (MGBG) | | Normal Patients | |
| --- | --- | --- | --- | --- | --- |
| Patient No. | $ED_{50}$ (μM) | Patient No. | $ED_{50}$ (μM) | Patient No. | $ED_{50}$ (μM) |
| 1 | 0.2 | 1 | 0.3 | 1 | 2 |
| 2 | 0.2 | 2 | 0.3 | 2 | 20 |
| 3 | 4 | 3 | 0.4 | 3 | 100 |
| 4 | 0.2 | 4 | 0.8 | 4 | 30 |
| 5 | 1 | 5 | 0.3 | 5 | 10 |
| 6 | 1 | 6 | 0.15 | 6 | 10 |
| 7 | 2 | 7 | 0.6 | 7 | 2 |
| 8 | 10 | 8 | 1.5 | 8 | 10 |
| 9 | 3 | 9 | 0.2 | 9 | 10 |
| 10 | 2 | 10 | 0.1 | | |
| 11 | 2 | | | | |
| 12 | 10 | | | | |
| 13 | 10 | | | | |
| Mean $ED_{50}$ | 3.5 μM | Mean $ED_{50}$ | 0.465 μM | Mean $ED_{50}$ | 21.5 μM |
| $P < 0.05$ | | $P < 0.05$ | | $P < 0.05$ | |

Example 6

This example shows that polyamine biosynthesis inhibitors (PBIs) show selective anti-HIV infected macrophage activity.

Elevated levels of CD16+ monocytes are observed in a number of disparate clinical conditions including HIV-associated neurological disease (HAND), amyotrophic lateral sclerosis (ALS), and Alzheimer's disease. Mononuclear cells from individuals with HIV infection, ALS, and healthy controls were evaluated for their sensitivity to PBIs.

Mononuclear cells were isolated from individuals with HIV infection, uninfected individuals or a patient with ALS and incubated in the absence or presence of increasing concentrations of the PBIs, MGBG (PA-001) and CG47. After five days in culture under non-adherent conditions cells were isolated stained with antibodies to CD14+ and CD16+ and counted by flow cytometry using a FACSCAN (BD-biosciences). The fraction of CD14+ monocytes that expressed CD16 was determined and compared to levels seen in the absence of drug.

Figure 5:
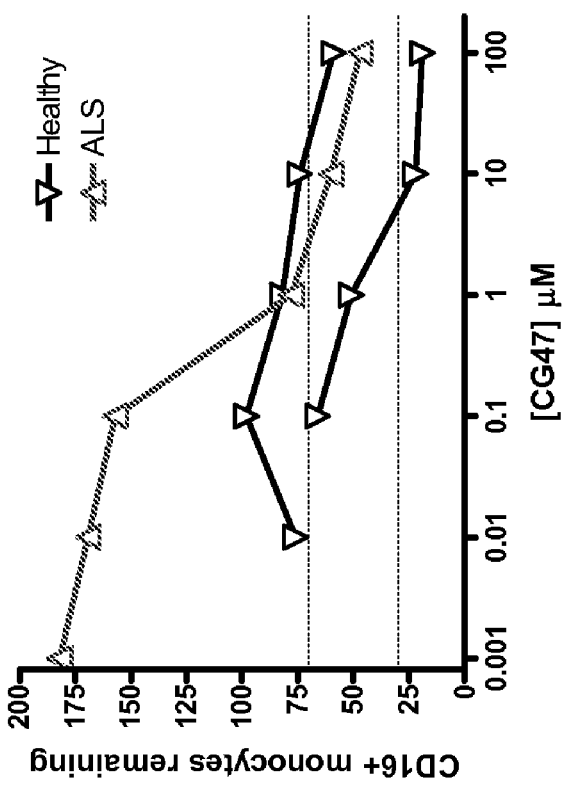
FIG. 5 shows the killing of CD14+/16+ monocytes by polyamine biosynthesis inhibitors (PBIs), PA-001 (MGBG) and CG47. Monocytes were isolated from individuals with HIV infection, uninfected individuals or a patient with ALS and incubated in the presence of increasing concentrations of PA-001 and CG47.
Figure 5:
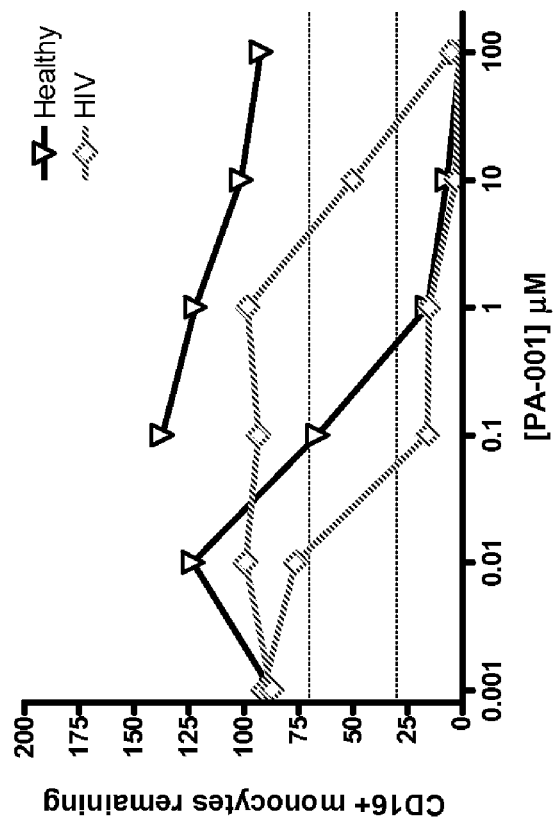

Typical results are shown in FIG. 5. Cells treated with MGBG (PA-001) showed 70% or greater reduction in CD16+ monocytes at concentrations of 1 μM. Those samples that were relatively resistant to PBIs required 100 μM or more of drug to achieve similar levels of killing. Most samples that were sensitive to CG47 exhibited 70% or greater reductions in levels of CD16+ monocytes with little or no changes in lymphocyte levels at a CG47 concentration of 10 μM or less. Samples that exhibited 70% or greater killing at 10 μM of drug were classified as sensitive to PBIs. Overall 65% to 80% of samples from individuals with HAND were sensitive (>70% killing with 10 μM PBI or less) to PBIs.

Figure 6:
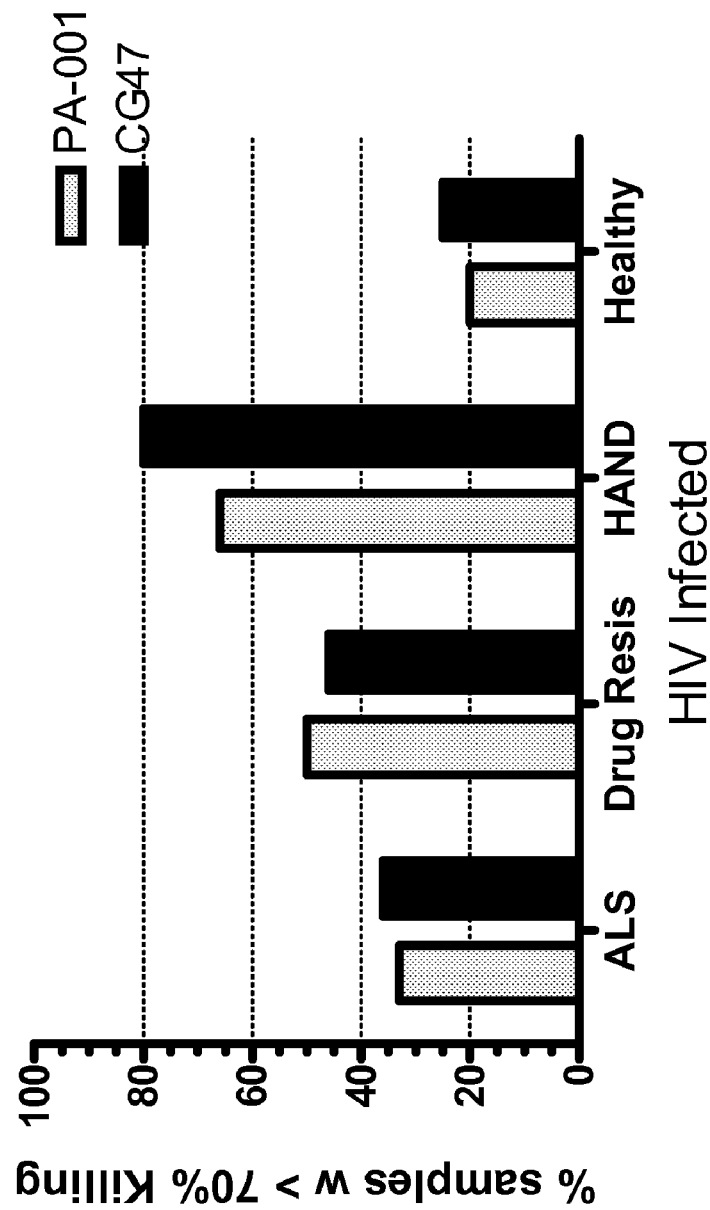
FIG. 6 shows the in vitro killing of CD16+ monocytes by disease. Amongst the groups tested healthy controls had the lowest number of monocyte samples sensitive to PBIs and individuals with HIV-associated neurological disease (HAND) had the greatest number.

The overall results with mononuclear cells from HIV infected individuals, ALS patients, and healthy controls are shown in FIG. 6. FIG. 6 shows the percentage of samples from individuals with the indicated diseases that exhibited 70% or greater killing of CD16+ monocytes in the presence of 10 μM of the indicated PBI after five days in culture. The number of mononuclear cell samples evaluated in each category were as follows: ALS with PA-001 (MGBG)=6, and with CG47=28. Drug resistant HIV with PA-001=22, and with CG47=48. HAD with PA-001=9, and with CG47=5. Healthy with PA-001=24, and with CG47=15.

As seen in FIG. 6, among the groups tested, healthy controls had the lowest number of mononuclear cell samples sensitive to PBIs and individuals with HAND had the greatest number. Further, FIG. 6 also shows that both PBIs, MGBG (PA-001) and CG47, were approximately equivalently effective.

Example 7

This example demonstrates the ability of the PBI MGBG (PA-001) to decrease HIV proviral load in CD14+ cells.

Mononuclear cells from HIV infected individuals were isolated and exposed to PA-001 in culture under non-adherent conditions for five days. The cells were then separated into CD3+ and CD14+ fractions via antibody-coated magnetic beads using a Miltenyi apparatus. The "-/-" samples represent flow thru after CD3+ and CD14+ cells were removed. Genomic DNA was prepared and then amplified with HIV specific primers and primers homologous to the single copy gene cJun. Results with HIV specific primers were normalized to those obtained with cJun. The results from multiple HIV infected individuals are presented in FIG. 7.

Figure 7:
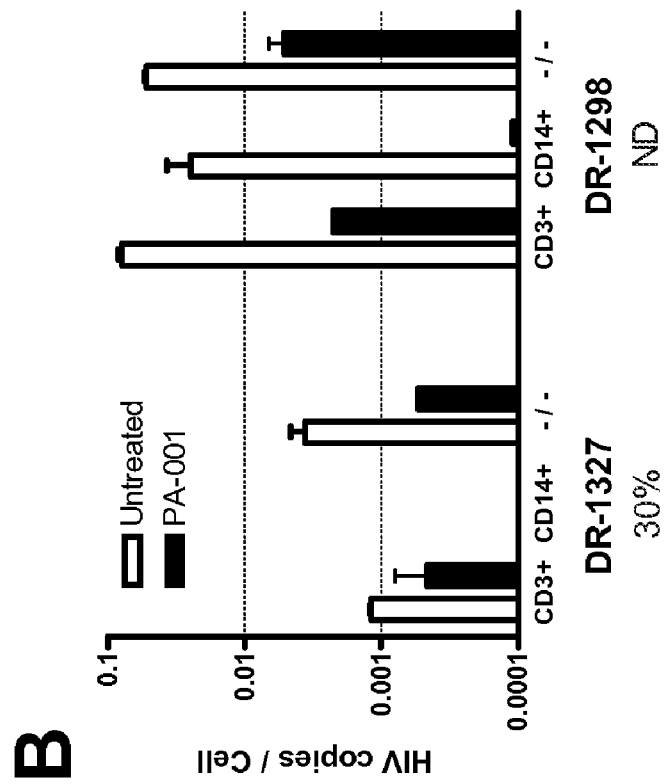
FIG. 7 shows the reduction in HIV proviral load after exposure to MGBG (PA-001) in vitro. Treatment with MGBG resulted in a significant reduction in HIV proviral DNA load.
Figure 7:
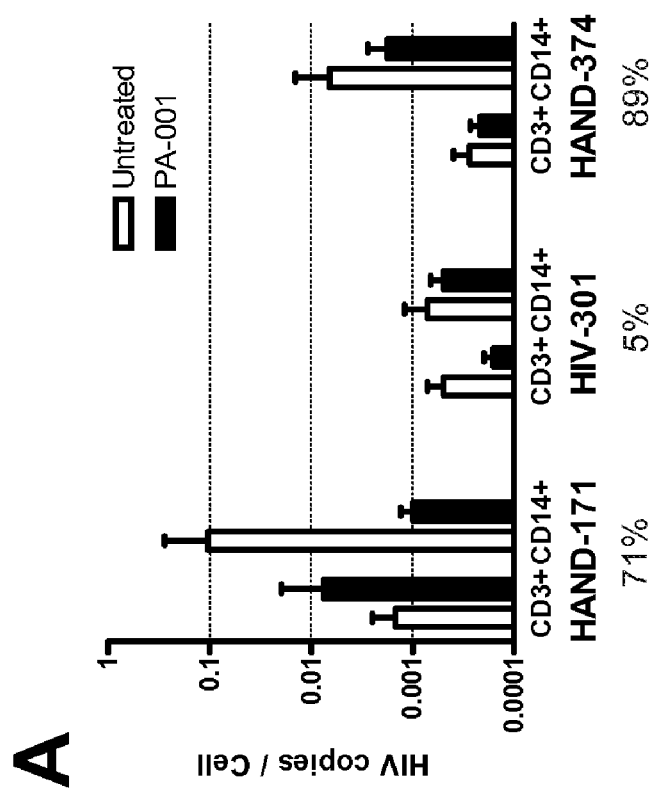

The number of HIV DNA copies per cellular DNA equivalent after exposure of mononuclear cell cultures from HIV infected individuals to PA-001 under non-adherent conditions for five days is shown in FIG. 7. Results with HIV specific primers were normalized to those obtained with cJun. Each bar represents the mean of three separate determinations. The error bar indicates one standard deviation from the mean. The numbers under the sample designations indicate the % of CD16+ monocytes killed by PA-001. ND=not done. Sample DR-1327 did not have any detectable HIV DNA in its CD14+ cells.

As can be seen from FIG. 7, treatment with MGBG (PA-001) resulted in significant decreases in HIV proviral load in CD14+ cells. The yield of HIV DNA in T cells was variable, but generally decreased slightly. FIG. 7B shows that PA-001 was effective in reducing HIV proviral load in cells that neither bound to CD14 or CD3 antibodies.

Example 8

This example shows the ability of MGBG (PA-001) to kill cultured rhesus macaque monocytes in vitro.

Dose response experiments with MGBG were performed to assess its ability to kill CD14+ CD16+ monocytes in non-adherent PBMC cultures. A dose-dependent decrease by MGBG of such cells cultured for five days in vitro was seen (see FIG. 8).

Figure 8:
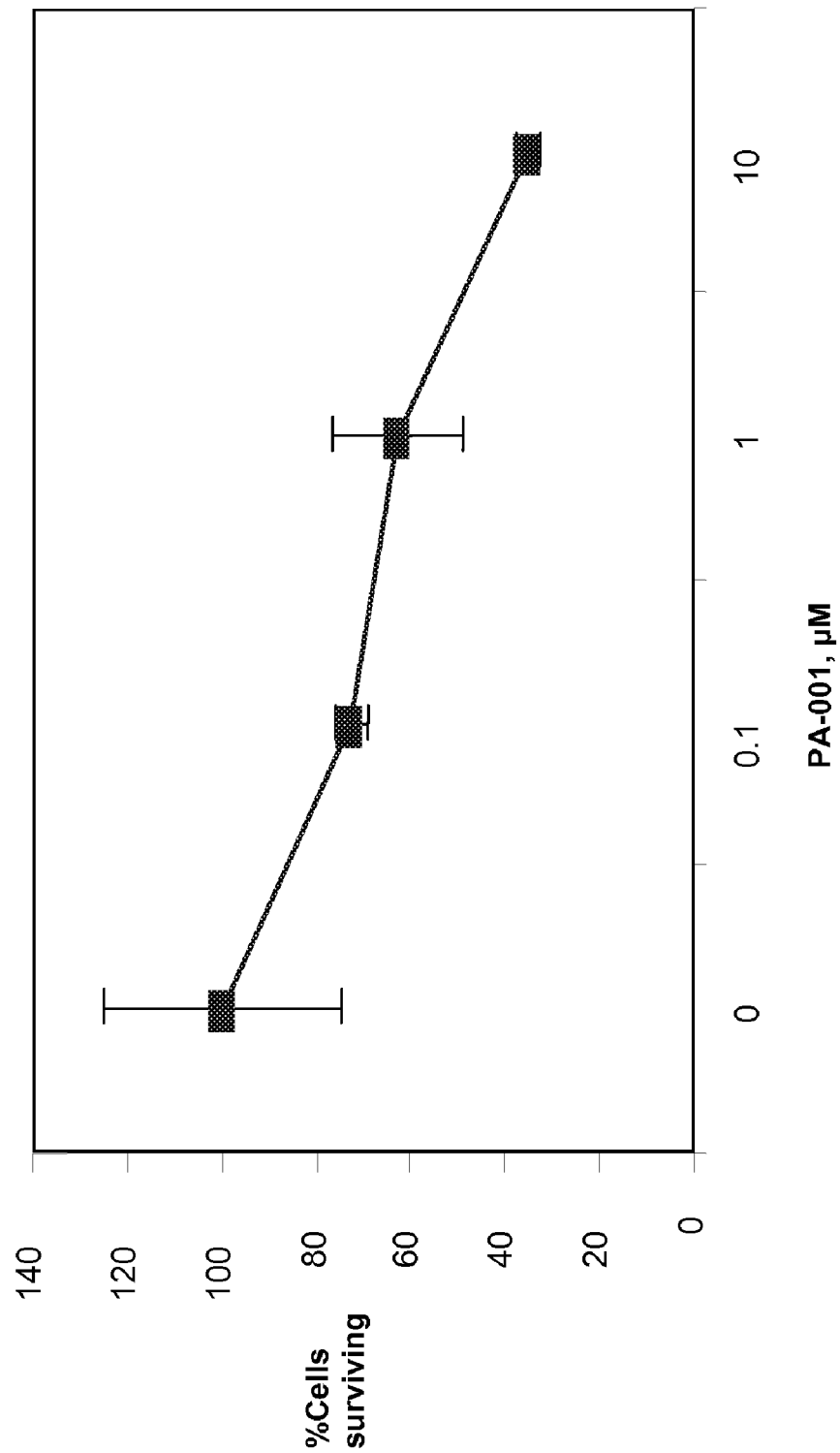
FIG. 8 is a graph showing the dose-dependent in vitro killing of cultured monkey monocytes with MGBG (PA-001).

A dose-dependent in vitro killing of cultured monkey (n=4) monocytes treated with PA-001 is shown in FIG. 8. As seen in the figure, 80% of activated monocytes were killed in a five-day assay at 10 µM of PA-001 (MGBG).

Example 9

This example demonstrates the depletion of CD14+CD16+ monocytes in the blood of SIV-infected, CD8-depleted animals treated with MGBG (PA-001).

For these experiments, rhesus macaques were infected with SIVmac251 and depleted of CD8+ T lymphocytes by administration of a humanized CD8-depleting antibody. This resulted in a rapid depletion of CD8+ T lymphocytes and a very rapid viral infection with a short time course to AIDS. These monkeys were then treated with escalating doses of MGBG.

The animals were treated with MGBG (PA-001) beginning five days post infection (p.i.) with 200 mg/m$^2$ PA-001, and then treated 7 and 14 days later with 300 mg/m$^2$ and 400 mg/m$^2$, respectively of PA-001. SIV-infected, CD8-depleted animals that were not treated with PA-001, showed a peak in the percentage and absolute number of CD14+CD16+ monocytes soon after infection. In contrast, PA-001 treated animals did not have increased monocytes, and in fact, had decreased levels of CD14+CD16+ monocytes, that were, very quickly after the 400 mg/m$^2$ treatment, depleted below detectable levels by day 21 p.i. These results are summarized in FIG. 9.

Figure 9:
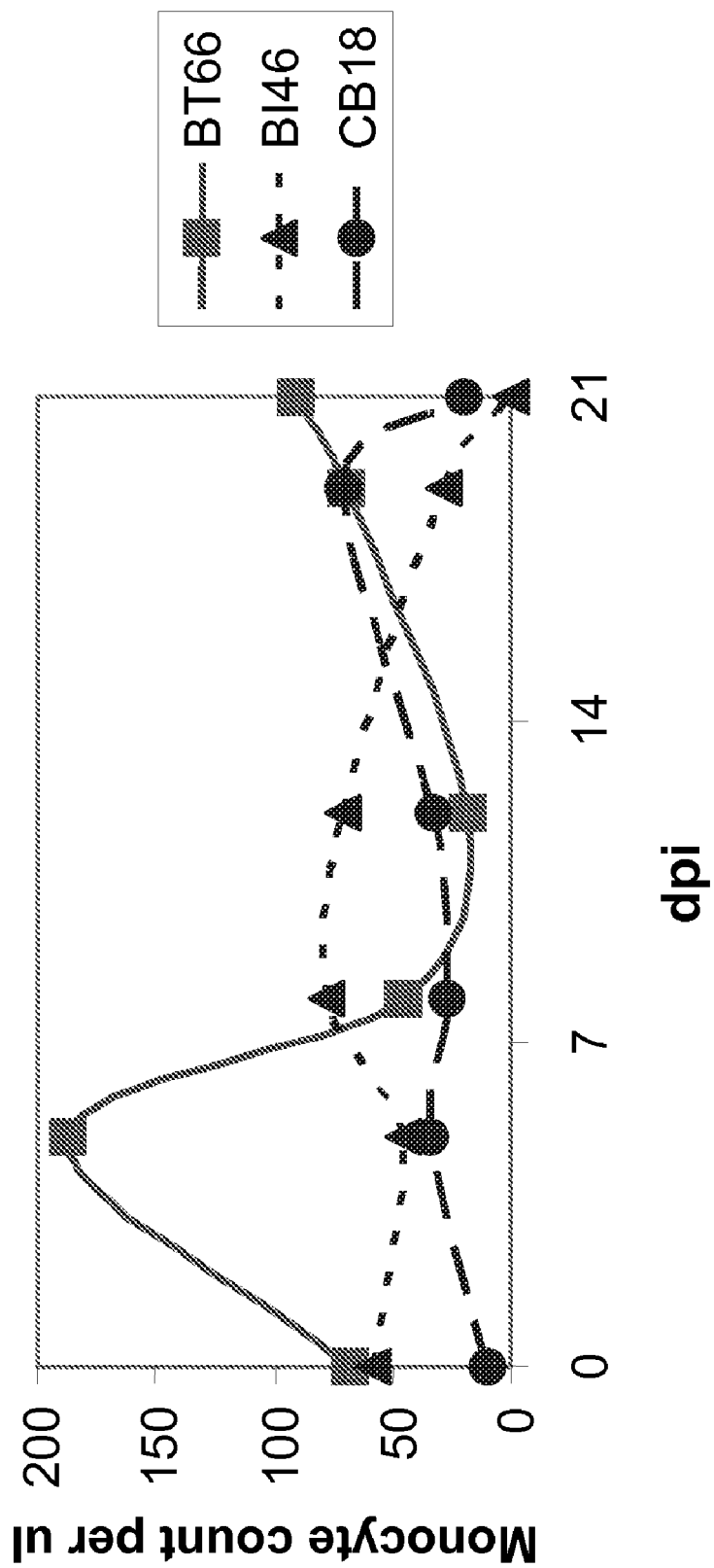
FIG. 9 shows the depletion of CD14+CD16+ monocytes in the blood of SIV-infected, CD8-depleted animals treated with MGBG (PA-001).

As can be seen in FIG. 9, CD8-depleted animals treated with PA-001 (BI46 and CB18) did not show an increase in the number of CD14+CD16+ monocytes soon after infection, whereas the untreated animal, BT66, did. Further detailed flow cytometric analysis revealed that CD14+CD16+ monocyte populations were the first population of monocytes targeted by the drug (data not shown). Analysis of plasma virus in these animals did not show significant differences between the PA-001 animals and control.

Example 10

This example demonstrates the effect of MGBG (PA-001) in decreasing the number of activated monocytes in the lymph nodes of MGBG treated animals.

Figure 10:
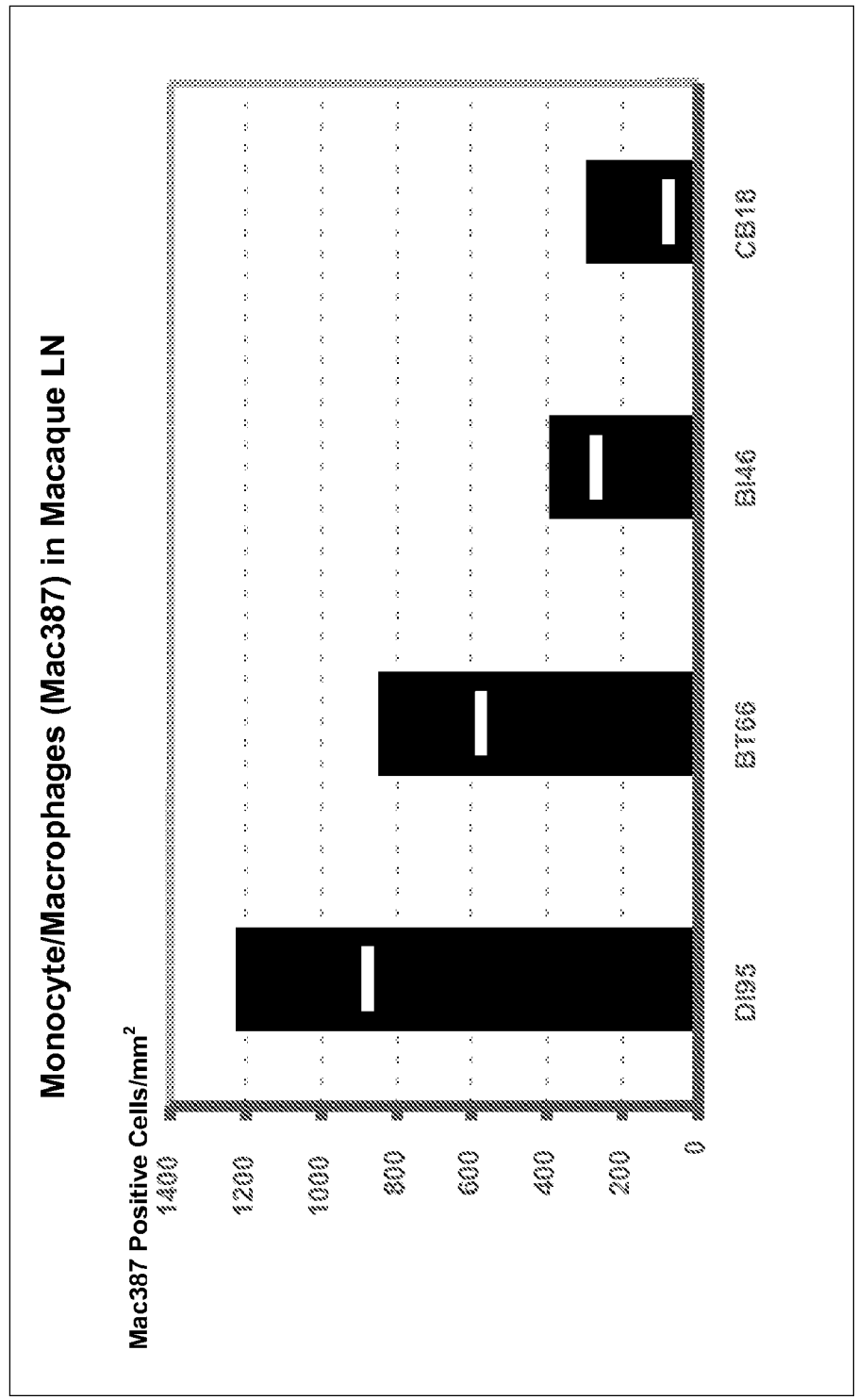
FIG. 10 shows the effect of MGBG (PA-001) in decreasing the number of activated monocytes in the lymph nodes of MGBG treated animals.

Analysis of lymph nodes from MGBG treated animals, compared to the non treated animal showed a significant decrease in the number of activated (MAC387+) monocytes. FIG. 10 shows the depletion of monocytes in the lymph node of PA-001 (MGBG) treated animals (BI46 and CB18). Immunohistochemical detection of newly infiltrated monocyte/macrophages stained with Mac387 showed a 50-80% decrease in cell number in PA-001 treated animals as compared to untreated animals.

Further, preliminary histopathological analysis showed that the SIVmac251-infected, CD8-depleted animal that was not PA-001 treated, had perivascular cuffs with productive viral replication in the CNS at 21 days p.i. In contrast, the PA-001 treated animals did not have perivascular cuffs or detectable virus at the same time point as the non treated control (data not shown).

Example 11

This example further demonstrates that untreated monkeys had higher counts of total monocytes and CD14+CD16+ monocytes as compared to MGBG treated monkeys.

Figure 11:
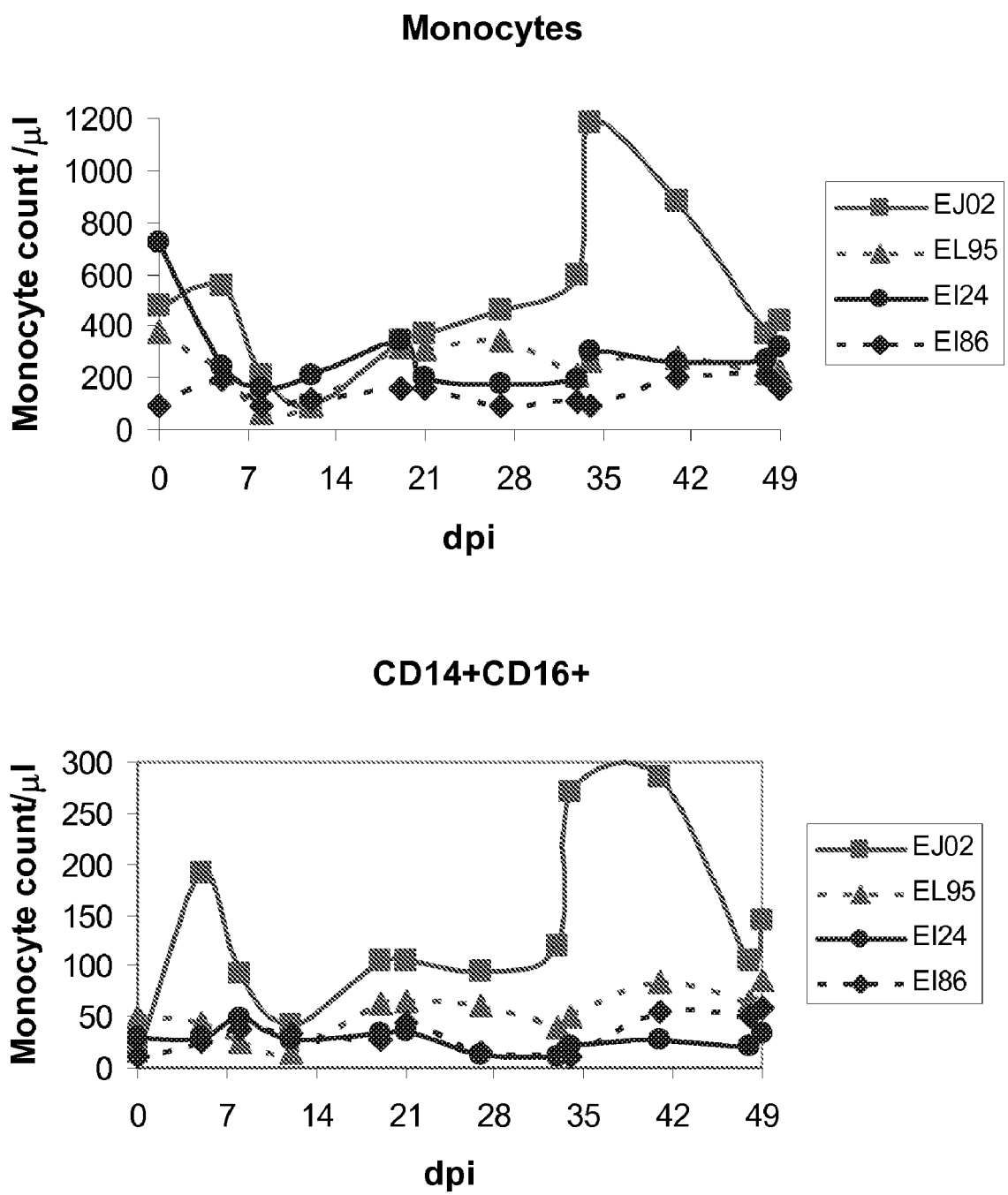
FIG. 11 shows the selective depletion of CD14+CD16+ monocytes in MGBG (PA-001) treated monkeys. SIV infected, CD8 depleted animals without MGBG treatment had higher counts of total monocytes and CD14+CD16+ monocytes.

These experiments once again used SIVmac251-infected, CD8-depleted animals, and again treatment was initiated at five days p.i. For this experiment, however, 250 mg/m$^2$ PA-001 (MGBG) was used and the animals were treated on alternate weeks, as is done in humans. Two animals were SIVmac251-infected, CD8-depleted, and PA-001 treated, and two were not drug treated, SIVmac251-infected, CD8-depleted controls. As of the time this study was conducted, the treated animals had received four doses of PA-001 and lived past day 55. In contrast, the non-treated animals developed AIDS and SIV encephalitis (SIVE) and in fact, one of the CD8-depleted, non-treated animals had died of AIDS and SIVE and the second non PA-001 treated animal was scheduled for sacrifice due to AIDS. Similar to the results of the previous example, the PA-001 treated animals had lower absolute numbers of total monocytes (FIG. 11). In addition, detailed flow cytometry showed significant decreases in the CD14+ and CD16+ monocyte populations of the PA-001 treated animals (data not shown).

The selective depletion of CD14+CD16+ monocytes in PA-001 treated monkeys, EI24 and EI86 is shown in FIG. 11. SIV-infected, CD8-depleted animals without PA-001 treatment (EJ02 and EL95) had higher counts of total monocytes (top) and the CD14+CD16+ subset (bottom). In fact, one of the untreated animals (EJ02) died of AIDS and SIVE at day 55 p.i.

Example 12

This example illustrates the complete removal of SIV DNA from the macrophages of a MGBG (PA-001) treated animal.

Rhesus macaques similar to those described in Example 9 were used for these studies. An SIVmac251-infected, CD8-depleted monkey was treated with PA-001 (MGBG) beginning five days p.i. with 200 mg/m² PA-001, and then treated 7 and 14 days later with 300 mg/m² and 400 mg/m², respectively of PA-001. A control monkey was SIVmac251-infected and CD8-depleted, but not treated with PA-001. Blood macrophages from control and treated monkeys were sorted every week into three subsets: CD14+/16−, CD14+/16+ and CD14−/16+ where CD14− indicates a low level of CD14 expression. Quantitative SIV PCR analysis of the sorted subsets was subsequently performed. The result of this study shows that the PA-001-treated monkey no longer had any detectable SIV DNA after the first and second dose of PA-001 in vivo as compared to the control animal which had SIV DNA in all of the monocyte subsets.

Figure 12:
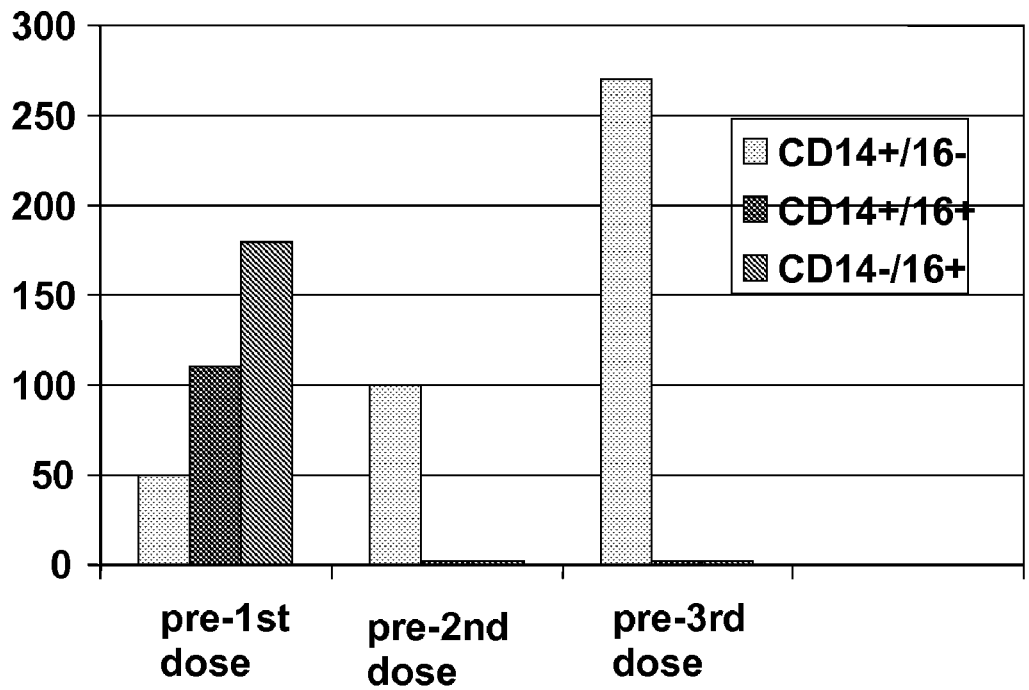
FIG. 12 shows the complete removal of SIV DNA from the macrophages of a MGBG (PA-001) treated animal after the first and second dose of MGBG.
Figure 12:
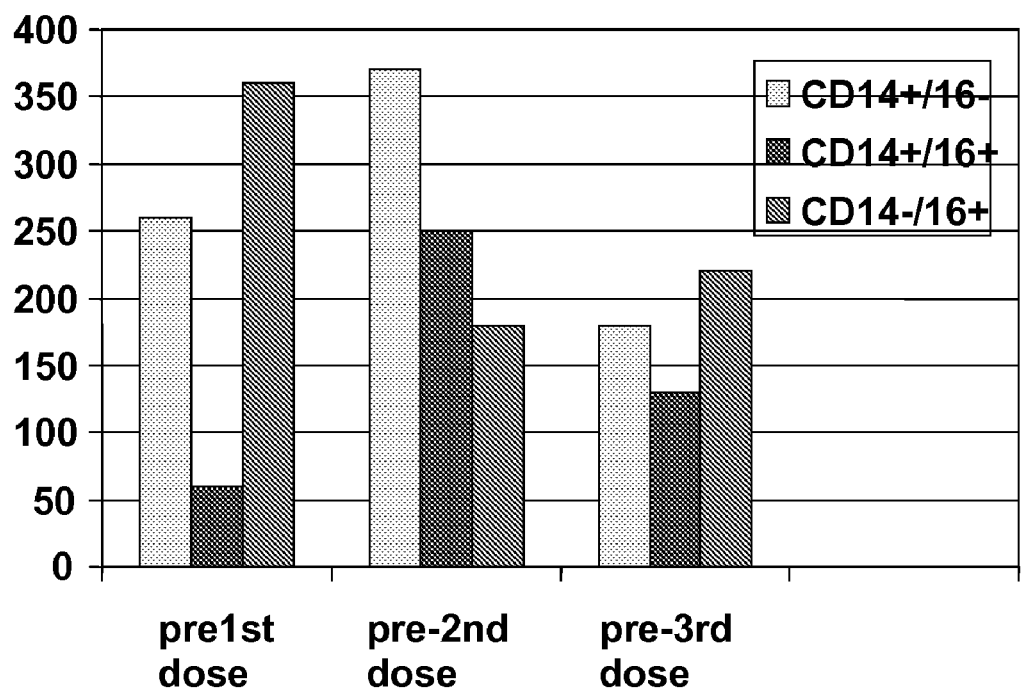

As seen in FIG. 12, the PA-001-treated monkey showed no detectable level of CD16+ DNA after the first and second dose (pre-$2^{nd}$ dose and pre-$3^{rd}$ dose, respectively) of treatment. In contrast, the control animal had SIV DNA in all of the monocyte subsets. This study unequivocally demonstrates the removal of SIV DNA reservoir cells in PA-001 treated monkeys.

For the purposes of this disclosure and unless otherwise specified, "a" or "an" means "one or more". All patents, applications, references and publications cited herein are incorporated by reference in their entirety to the same extent as if they were individually incorporated by reference.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

The invention has been described with reference to various specific and illustrative embodiments. However, it should be understood that many variations and modifications may be made while remaining within the spirit and scope of the invention.

What is claimed is:

1. A method of treating an immunodeficiency viral infection comprising reducing proviral load of a subject with the immunodeficiency viral infection by administering to the subject a therapeutically effective amount of a polyamine analog whereby reducing the proviral load in the subject, wherein the subject does not have AIDS-associated dementia or AIDS associated lymphoma, and wherein the polyamine analog is MGBG; a salt thereof; N,N' bis(3-ethylaminopropyl)-cis-but-2-ene-1,4-diamine tetrahydrochloride (CG47); or a salt thereof.

2. The method of claim 1, wherein the viral infection is selected from the group consisting of human immunodeficiency virus type 1 (HIV-1) infection, human immunodeficiency virus type 2 (HIV-2) infection, simian immunodeficiency virus (SIV) infection, and feline immunodeficiency virus (FIV) infection.

3. The method of claim 1, wherein the therapeutically effective amount of the polyamine analog reduces the proviral load in the subject by at least 80%.

4. The method of claim 1, wherein the therapeutically effective amount of the polyamine analog reduces the proviral load in blood CD14+ and CD16+ macrophages in the subject by at least 80%.

5. The method of claim 1, wherein the therapeutically effective amount of the polyamine analog is from about 10 to about 1100 mg/m².

6. The method of claim 1, wherein the therapeutically effective amount of the polyamine analog is administered daily, once per week, once every other week, or once per month.

7. The method of claim 5, wherein the therapeutically effective amount of the polyamine analog is administered for at least four weeks.

8. The method of claim 1, wherein the polyamine analog is administered in combination with at least one antiviral agent.

9. The method of claim 8, wherein the at least one antiviral agent is an antiretroviral agent selected from the group consisting of nucleoside reverse transcriptase inhibitors, nucleotide reverse transcriptase inhibitors, non-nucleoside reverse transcriptase inhibitors, protease inhibitors, entry inhibitors, integrase inhibitors, gp41 inhibitors, CXCR4 inhibitors, and gp120 inhibitors.

10. The method of claim 8, wherein at least one antiviral agent is an antiretroviral agent selected from the group consisting of amdoxovir, elvucitabine, alovudine, racivir, phosphazide, fozivudine tidoxil, apricitibine, amdoxovir, zidovudine, didanosine, lamivudine, stavudine, zalcitabine, emtricitabine, abacavir, tenofovir, adefovir, capravirine, emivirine, calanolide A, etravirine, efavirenz, nevirapine, delavirdine, amprenavir, tipranavir, lopinavir, fosamprenavir, atazanavir, darunavir, brecanavir, mozenavir, indinavir, nelfinavir, ritonavir, saquinavir, SP01A, curcumin, derivatives of chicoric acid, 3,5-dicaffeoylquinic acid, aurintricarboxylic acid, caffeic acid phenethyl ester, tyrphostin, quercetin, S-1360, zintevir, L-870812, L-870810, MK-0518, BMS-538158, GSK364735C, enfuvirtide, AMD-070, and BMS-488043, and any two or more combination thereof.

11. The method of claim 8, wherein the polyamine analog is administered in combination with a first nucleoside reverse transcriptase inhibitor, a non-nucleoside reverse transcriptase inhibitor, and a protease inhibitor.

12. The method of claim 8, wherein the polyamine analog is administered in combination with a first and second non-nucleoside reverse transcriptase inhibitor and a nucleoside reverse transcriptase inhibitor, wherein the first non-nucleotide reverse transcriptase inhibitor is different from the second non-nucleoside reverse transcriptase inhibitor.

13. The method of claim 8, wherein the antiviral agent is an agent that reduces the immunodeficiency viral load in T-cells.

14. The method of claim 13, wherein the agent that reduces the immunodeficiency viral load in T-cells is a T-cell activating cytokine, anti-CD3 antibody, or anti-CD45RO-toxin conjugate.

15. The method of claim 14, wherein the T-cell activating cytokine is IL-2, IL-6, TNF-α, or any two or more thereof.

16. The method of claim 13, wherein the polyamine analog is administered in combination with an antiviral agent or an agent that reduces viral load.

17. A method of treating an immunodeficiency viral infection comprising reducing proviral load of a subject with the immunodeficiency viral infection by administering to the subject a therapeutically effective amount of MGBG, or a salt thereof, whereby reducing the proviral load in the subject, wherein the subject does not have AIDS-associated dementia or AIDS associated lymphoma.

18. The method of claim 17, wherein the viral infection is selected from the group consisting of human immunodeficiency virus type 1 infection, human immunodeficiency virus type 2 infection, simian immunodeficiency virus infection, and feline immunodeficiency virus infection.

19. The method of claim 17, wherein the therapeutically effective amount of MGBG, or the salt thereof, reduces the proviral load in the subject by at least 80%.

20. The method of claim 17, wherein the therapeutically effective amount of MGBG, or the salt thereof, reduces the proviral load in blood CD14+ and CD16+ macrophages in the subject by at least 80%.

21. A method of treating a disease having a high proviral load comprising reducing proviral load in a subject infected with the disease by administering to the subject a therapeutically effective amount of MGBG or a salt thereof.

22. The method of claim 21, wherein the disease is HIV-1 infection or HIV-2 infection.

* * * * *